(12) United States Patent
Green et al.

(10) Patent No.: US 11,401,380 B2
(45) Date of Patent: Aug. 2, 2022

(54) POLY(β-AMINO ESTER)-CO-POLYETHYLENE GLYCOL (PEG-PBAE-PEG) POLYMERS FOR GENE AND DRUG DELIVERY

(71) Applicant: THE JOHNS HOPKINS UNIVERSITY, Baltimore, MD (US)

(72) Inventors: Jordan Green, Nottingham, MD (US); Jayoung Kim, Baltimore, MD (US); Stephany Tzeng, Somerville, MA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1255 days.

(21) Appl. No.: 15/561,869

(22) PCT Filed: Mar. 28, 2016

(86) PCT No.: PCT/US2016/024525
§ 371 (c)(1),
(2) Date: Sep. 26, 2017

(87) PCT Pub. No.: WO2016/154622
PCT Pub. Date: Sep. 29, 2016

(65) Prior Publication Data
US 2018/0112038 A1 Apr. 26, 2018

Related U.S. Application Data

(60) Provisional application No. 62/138,694, filed on Mar. 26, 2015.

(51) Int. Cl.
| | | |
|---|---|---|
| *A61K 47/60* | (2017.01) | |
| *A61K 47/69* | (2017.01) | |
| *A61K 9/107* | (2006.01) | |
| *A61P 31/00* | (2006.01) | |
| *A61K 48/00* | (2006.01) | |
| *C08G 63/672* | (2006.01) | |
| *C08G 63/685* | (2006.01) | |
| *C08L 71/02* | (2006.01) | |
| *A61P 35/00* | (2006.01) | |
| *C08G 81/00* | (2006.01) | |
| *C12N 15/113* | (2010.01) | |
| *C08G 73/02* | (2006.01) | |
| *A61K 47/59* | (2017.01) | |
| *C08G 63/688* | (2006.01) | |
| *C08G 63/91* | (2006.01) | |
| *C12N 7/00* | (2006.01) | |
| *C08G 75/12* | (2016.01) | |
| *C12N 15/88* | (2006.01) | |

(52) U.S. Cl.
CPC ........ *C08G 73/0253* (2013.01); *A61K 9/1075* (2013.01); *A61K 47/59* (2017.08); *A61K 47/60* (2017.08); *A61K 47/6907* (2017.08); *A61K 47/6935* (2017.08); *A61K 48/0041* (2013.01); *A61P 31/00* (2018.01); *A61P 35/00* (2018.01); *C08G 63/672* (2013.01); *C08G 63/6856* (2013.01); *C08G 63/6886* (2013.01); *C08G 63/916* (2013.01); *C08G 73/024* (2013.01); *C08G 75/12* (2013.01); *C08G 81/00* (2013.01); *C08L 71/02* (2013.01); *C12N 7/00* (2013.01); *C12N 15/113* (2013.01); *C12N 15/88* (2013.01); *C08G 2261/126* (2013.01); *C08L 2205/05* (2013.01); *C12N 2310/14* (2013.01); *C12N 2310/351* (2013.01); *C12N 2320/32* (2013.01); *C12N 2710/16643* (2013.01)

(58) Field of Classification Search
CPC .. C08G 73/0253; C08G 73/024; C12N 15/88; C08L 71/02; A61K 47/60
See application file for complete search history.

(56) References Cited

U.S. PATENT DOCUMENTS

2008/0311040 A1\* 12/2008 Berry ..................... A61P 43/00
514/1.1

FOREIGN PATENT DOCUMENTS

| WO | 2010132879 A2 | 11/2010 |
|---|---|---|
| WO | 2014066811 A1 | 5/2014 |

OTHER PUBLICATIONS

Tzeng et al. (2013) Subtle changes to polymer structure and degradation mechanism enable highly effective nanoparticles for siRNA and DNA delivery to human brain cancer. Advanced Healthcare Materials, 2(3):468-480 (Year: 2013).\*

Min et al. (2010) Tumoral acidic pH-responsive MPEG-poly(β-amino ester) polymeric micelles for cancer targeting therapy. Journal of Controlled Release, 144:259-266 (Year: 2010).\*

Sawicki et al. (2014) Design of thiol-ene photoclick hydrogels using facile techniques for cell culture applications. Biomaterials Science, 2:1612-1626 (Year: 2014).\*

Shenoy et al. (2006) Surface functionalization of gold nanoparticles using hetero-bifunctional poly(ethylene glycol) spacer for intracellular tracking and delivery. International Journal of Nanomedicine, 1(1):51-57 (Year: 2006).\*

(Continued)

*Primary Examiner* — Neil P Hammell
(74) *Attorney, Agent, or Firm* — Casimir Jones, S.C.; Jeffrey W. Childers

(57) ABSTRACT

Polyethylene glycol (PEG)-b-poly(β-amino ester) (PBAE) co-polymers (PEG-PBAE) and blends of PEG-PBAEs and PBAEs and their use for delivering drugs, genes, and other pharmaceutical or therapeutic agents safely and effectively to different sites in the body and to different cells, such as cancer cells, are disclosed.

21 Claims, 27 Drawing Sheets

(56) References Cited

OTHER PUBLICATIONS

Kim et al. (2006) pH-Responsive PEG-Poly(b-amino ester) Block Copolymer Micelles with a Sharp Transition. Macromolecular Rapid Communications, 27:447-451 (Year: 2006).*
Shenoy et al. (2005) Poly(ethylene oxide)-Modified Poly(beta-amino ester) Nanoparticles as a pH-Sensitive System for Tumor-Targeted Delivery of Hydrophobic Drugs. 1. In Vitro Evaluations. Molecular Pharmaceutics, 2(5):357-366 (Year: 2005).*
Ko et al. (2007) Tumoral acidic extracellular pH targeting of pH-responsive MPEG-poly (β-amino ester) block copolymer micelles for cancer therapy. Journal of Controlled Release, 123:109-115 (Year: 2007).*
Tzeng et al., Biomaterial-mediated cancer-specific DNA delivery to liver cell cultures using synthetic poly(beta-amino esters), J Biomed Mater Res A, 101 (2013): 1837-45.
Nguyen et al., pH-sensitive and bioadhesive poly(β-amino ester)-poly(ethylene glycol)-poly(β-amino ester) triblock copolymer hydrogels with potential for drug delivery in oral mucosal surfaces, Polymer, 2009, vol. 50, No. 22, pp. 5205-5210.
Song et al., Tunable pH-sensitive Poly(p-amino esters) Synthesized from Primary Amines and Diacrylates for Intracellular Drug Delivery, Macromol. Biosci., 2012, 12:1375-1383.
Kim et al., pH-Responsive PEG-Poly(beta-amino ester) Block Copolymer Micelles with a Sharp Transition, Macromolecular Rapid Communications. 27(6), 2006, pp. 447-451.
Rodriguez et al., Small cell lung cancer: past, present, and future, Curr Oncol Rep, 12 (2010):327-34.
Paumier et al., Radiotherapy in small-cell lung cancer: where should it go?, Lung Cancer, 69(2010): 133-40.
Siegel et al., Cancer statistics, 2012, CA: A Cancer Journal for Clinicians, 62 (2012):10-29.
Brade et al., Scheduling of radiation and chemotherapy for limited-stage small-cell lung cancer: repopulation as a cause of treatment failure?, J Clin Oncol, 24 (2006): 1020-2.
Hollon, Researchers and regulators reflect on first gene therapy death, Nat Med, 6(2000):6.
Pack et al., Design and development of polymers for gene delivery, Nat Rev Drug Discov, 4 (2005):581-93.
Anderson et al., Structure/property studies of polymeric gene delivery using a library of poly(beta-amino esters), Mo Tier, 11(2005)1426-34.
Bhise et al., Evaluating the potential of poly(beta-amino ester) nanoparticles for reprogramming human fibroblasts to become induced pluripotent stem cells, Int J Nanomedicine, 8 (2013):4641-58.
Cho et al., Therapeutic angiogenesis using genetically engineeredhuman endothelial cells, J Control Release, 160 (2012):515-24.
Tzeng et al., Subtle changes to polymer structure and degradation mechanism enable highly effective nanoparticles for siRNA and DNA delivery to human brain cancer, Adv Healthc Mater, 2 (2013):468-80.
Vandenbrouke et al., Prolonged gene silencing in hepatoma cells and primary hepatocytes after small interfering RNA delivery with biodegradable poly(beta-amino esters), J Gene Med, 10 (2008):783-94.
Bishop et al., The effect and role of carbon atoms in poly(beta-amino ester)s for DNA binding and gene delivery, J Am Chem Soc, 135(2013):6951-7.
Sunshine et al., Uptake and transfection with polymeric nanoparticles are dependent on polymer end-group structure, but largely independent of nanoparticle physical and chemical properties, Mol Pharm, 9 (2012):3375-83.
Harris et al.,Tissue-specific gene delivery via nanoparticle coating, Biomaterials, 31 (2010):998-1006.
Harris et al., Effect of pegylation on pharmaceuticals, Nat Rev Drug Discov, 2 (2003):214-21.
Owens et al., Opsonization, biodistribution, and pharmacokinetics of polymeric nanoparticles, Int J Pharm, 307 (2006):93-102.
Salmaso et al., Stealth Properties to Improve Therapeutic Efficacy of Drug Nanocarriers, Journal of Drug Delivery, vol. 2013, Article ID 374252, 19 pages, 2013.
Sunshine et al., Effects of base polymer hydrophobicity and end-group modification on polymeric gene delivery, Biomacromolecules, 12 (2011):3592-600.
Vandenburg et al., Synthesis of (Bio)-Degradable Poly(p-thioester)s via Amine Catalyzed Thiol-ene Click Polymerization, Macromolecular Chemistry and Physics, 213 (2012):2611-7.
Mangraviti et al., Polymeric nanoparticles for nonviral gene therapy extend brain tumor survival in vivo, ACS Nano, 9 (2015):1236-49.
Kim et al., Differential polymer structure tunes mechanism of cellular uptake and transfection routes of poly(beta-amino ester) polyplexes in human breast cancer cells, Bioconjug Chem, 25 (2014):43-51.
Boucher et al., Differential ganciclovir-mediated cytotoxicity and bystander killing in human colon carcinoma cell lines expressing herpes simplex virus thymidine kinase, Hum Gene Ther, 9 (1998):801-14.
Shalev et al., Suicide gene therapy toxicity after multiple and repeat injections in patients with localized prostate cancer, J Urol, 163 (2000):1747-50.
Rubsam et al., Cytotoxicity and accumulation of ganciclovir triphosphate in bystander cells cocultured with herpes simplex virus type 1 thymidine kinase-expressing human glioblastoma cells, Cancer Res, 59 (1999):669-75.
Tomicic et al., Ganciclovir-induced apoptosis in HSV-1 thymidine kinase expressing cells: critical role of DNA breaks, Bcl-2 decline and caspase-9 activation, Oncogene, 21 (2002):2141-53.
Steichen et al., A review of current nanoparticle and targeting moieties for the delivery of cancer therapeutics, Eur J Pharm Sci, 48 (2013):416-27.
Boeckle et al., Purification of polyethylenimine polyplexes highlights the role of free polycations in gene transfer, J Gene Med, 6 (2004):1102-11.
Park et al., Degradable polyethylenimine-alt-poly(ethylene glycol) copolymers as novel gene carriers, J Control Release, 105 (2005):367-80.
Kim et al., Targeted polymeric nanoparticles for cancer gene therapy, J Drug Target, 23 (2015):627-41.
Green et al., A combinatorial polymer library approach yields insight into nonviral gene delivery. Acc Chem Res, 41 (2008):749-59.
Ko et al., Tumoral acidic extracellular pH targeting of pH-responsive MPEG-poly (beta-amino ester) block copolymer micelles for cancer therapy, J Controlled Release, 2007, 123:109-115.
Mishra et al., PEGylation significantly affects cellular uptake and intracellular trafficking of 10 non-viral gene delivery particles, Eur J Cell Biol, 83 (2004):97-111.
Kamat et al., Poly(beta-amino ester) nanoparticle delivery of P53 has activity against small cell lung cancer in vitro and in vivo, Mol Cancer Ther, 12 (2013):405-15.
Gerrero-Cazares et al., Biodegradable polymeric nanoparticles show high efficacy and specificity at DNA delivery to human glioblastoma in vitro and in vivo, ACS Nano, 8 (2014):5141-53.
International Search Report and Written Opinion for Application No. PCT/US2016/024525 dated Jul. 6, 2016 (12 pages).

* cited by examiner

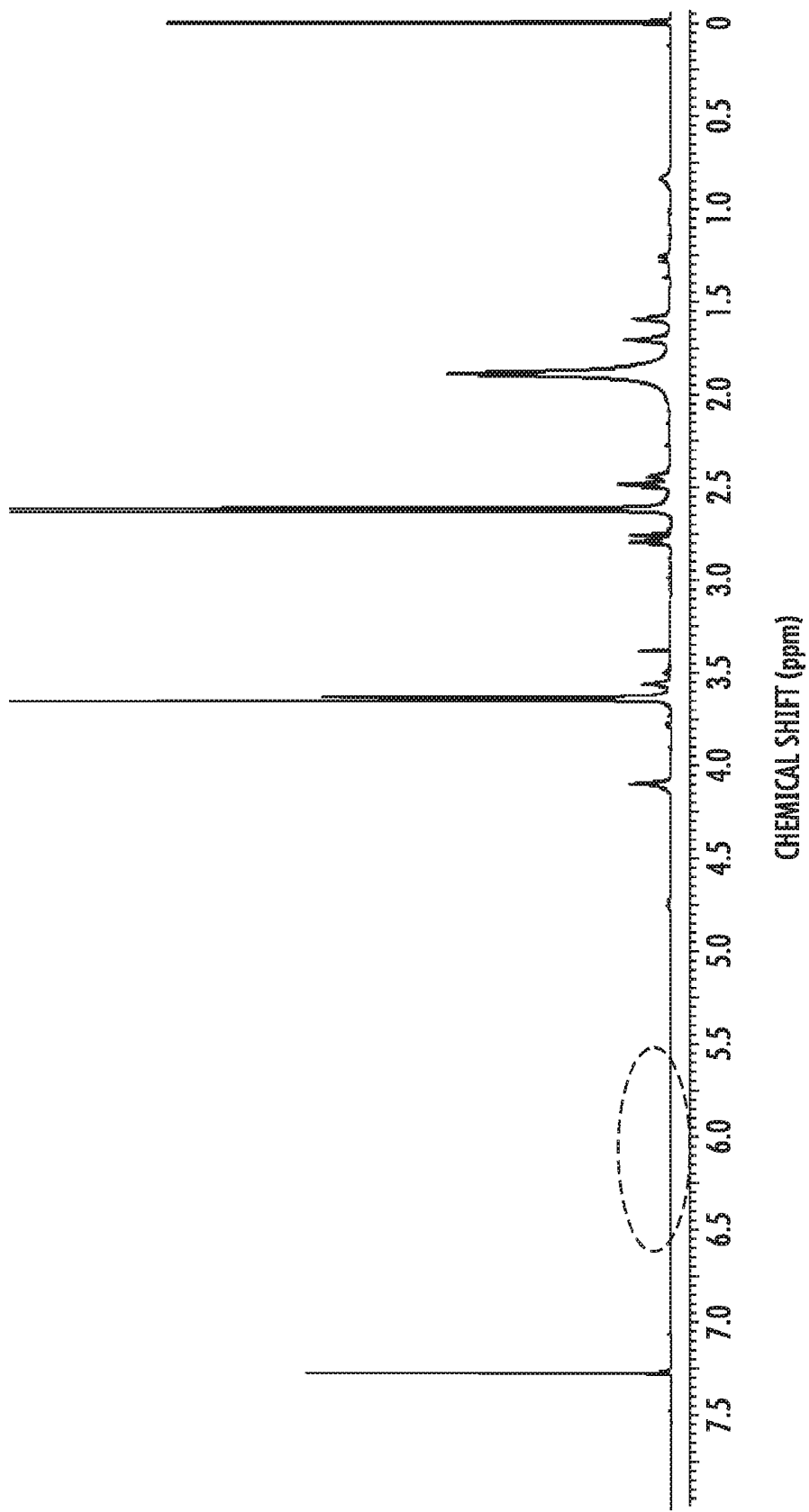

POLY(β-AMINO ESTER)-CO-POLYETHYLENE GLYCOL (PEG-PBAE-PEG) POLYMERS FOR GENE AND DRUG DELIVERY

CROSS-REFERENCE TO RELATED APPLICATIONS

This application is a 35 U.S.C. § 371 National Stage Entry of International Application No. PCT/US16/024525 having an international filing date of Mar. 28, 2016, which claims the benefit of U.S. Provisional Application No. 62/138,694, filed Mar. 26, 2015, the contents of which is are incorporated herein by reference in their entirety.

FEDERALLY SPONSORED RESEARCH OR DEVELOPMENT

This invention was made with government support under R01-EB016721 awarded by the National Institutes of Health. The government has certain rights in the invention.

BACKGROUND

Non-viral vectors are widely investigated due to their ability to safely and effectively deliver exogenous genes and potentially cure diseases of genetic origin. Much of the ongoing research in the field also is dedicated to further optimize existing vectors for in vivo applications. The use of amphiphilic block copolymers as therapeutic modalities in cancer and other diseases has been extensively studied in recent years. Amphiphilic copolymers self-assemble to form micelles in an aqueous environment due to hydrophobic interactions. To this end, block-copolymer micelles are versatile drug carries that have properties that allow for controlled release and can accommodate functional modifications. Ko et al., *J. Controlled Release* (2007).

Poly(β-amino ester)s (PBAEs) are pH-sensitive, biodegradable polymers that have been widely investigated as both gene and drug delivery vectors. Song et al., *Macromol. Biosci.* (2012). The pH buffering capability of PBAEs, which results from the presence of tertiary amines in the PBAE structure, facilitates endosomal escape and hence intracellular delivery of therapeutics. Moreover, surface functionalization with neutrally charges, hydrophilic polyethylene glycol (PEG) molecules provides steric hindrance to prevent non-specific adsorption of proteins on the particles' surface. Green et al., *Acc. Chem. Res.* (2008); Salmaso and Caliceti, *J. Drug Delivery* (2013).

SUMMARY

In some aspects, the presently disclosed subject matter provides a polyethylene glycol (PEG)-b-poly(β-amino ester) (PBAE) co-polymer (PEG-PBAE) of Formula (I):

wherein: each n and n' is independently an integer from 1 to 10,000, 1 to 1,000, 1 to 100, 1 to 30, 5 to 20, 10 to 15, and 1 to 10; R is $C_2$ to $C_8$ substituted or unsubstituted linear or branched alkylene; and R' is $C_1$ to $C_5$ substituted or unsubstituted linear or branched alkylene, wherein each R and R' can independently be the same or different; and pharmaceutically acceptable salts thereof.

In other aspects, the presently disclosed subject matter provides a micelle comprising one or more of the presently disclosed polyethylene glycol (PEG)-b-poly(β-amino ester) (PBAE) co-polymers. In particular aspects, the micelle comprises a cargo, which in some aspects comprises one or more hydrophobic drugs.

In yet other aspects, the presently disclosed subject matter provides a particle comprising a blend of a polyethylene glycol (PEG)-b-poly(β-amino ester) (PBAE) co-polymer of Formula (I) and a poly(β-amino ester) (PBAE). In particular aspects, the blend comprises a cargo, which in some aspects comprises a drug or a gene. In yet more particular aspects, the cargo comprises DNA or siRNA.

In yet further aspects, the presently disclosed subject matter provides a method for preparing a polyethylene glycol (PEG)-b-poly(β-amino ester) (PBAE) co-polymer of Formula (I), the method comprising: (a) synthesizing an acrylate-terminated poly(β-amino ester) (PBAE) via Michael addition of a diacrylate monomer and a primary amine-containing monomer at a molar ratio; and (b) reacting the acrylate-terminated PBAE with a functionalized PEG molecule to form a polyethylene glycol (PEG)-b-poly(β-amino ester) (PBAE) co-polymer.

In other aspects, the presently disclosed subject matter provides a method for forming a polyplex comprising DNA or siRNA, the method comprising diluting a blend of a polyethylene glycol (PEG)-b-poly(β-amino ester) (PBAE) co-polymer and a poly(β-amino ester) (PBAE) in a solvent at a concentration at a weight-to-weight ratio with DNA or siRNA to form a polyplex comprising DNA or siRNA.

In yet further aspects, the presently disclosed subject matter provides a method for treating a disease or condition, the method comprising administering to a subject in need of treatment thereof, a compound of Formula (I) or a pharmaceutical composition thereof, comprising a pharmaceutical or therapeutic agent effective for treating the disease or condition.

In still yet further aspects, the presently disclosed subject matter provides a method for delivering a therapeutic agent to a cell, a specific cell line, a tissue, or an organism, the method comprising associating a pharmaceutical or therapeutic agent with a compound of Formula (I), or a pharmaceutical composition thereof, to form one or more particles, micelles, or polyplexes comprising the agent and compound of Formula (I), and administering the one or more particles or contacting the one or more particles with the cell, specific cell line, tissue or organism.

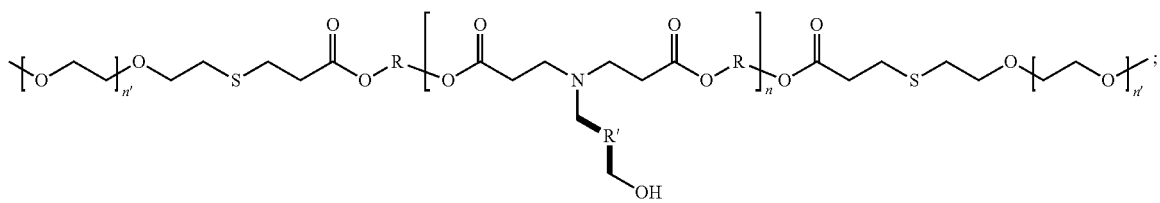

(I)

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
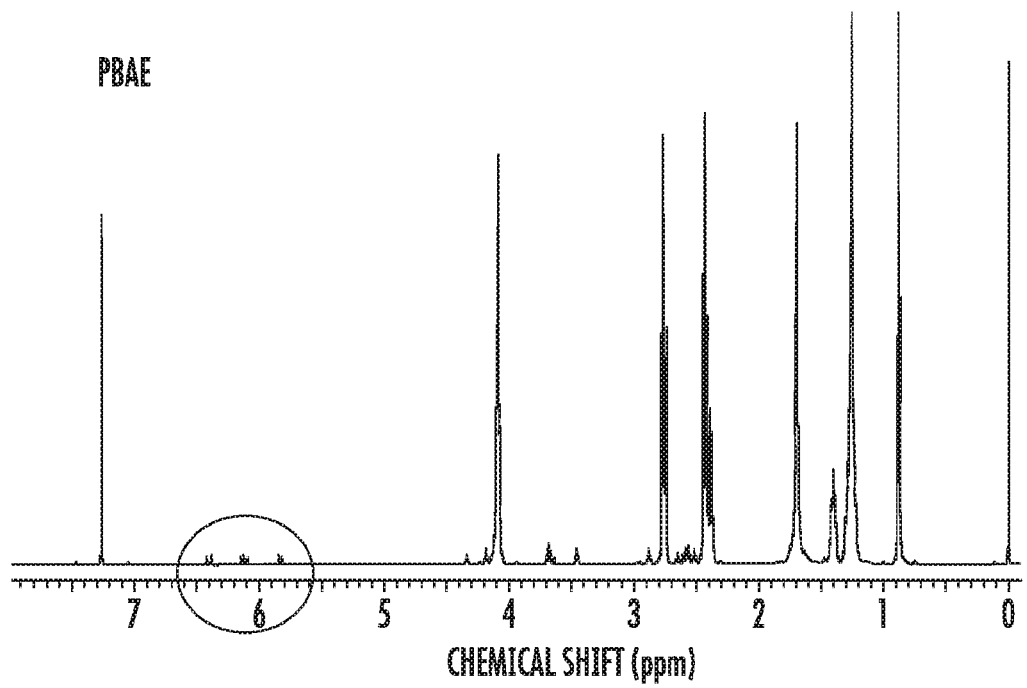
Figure 1A:
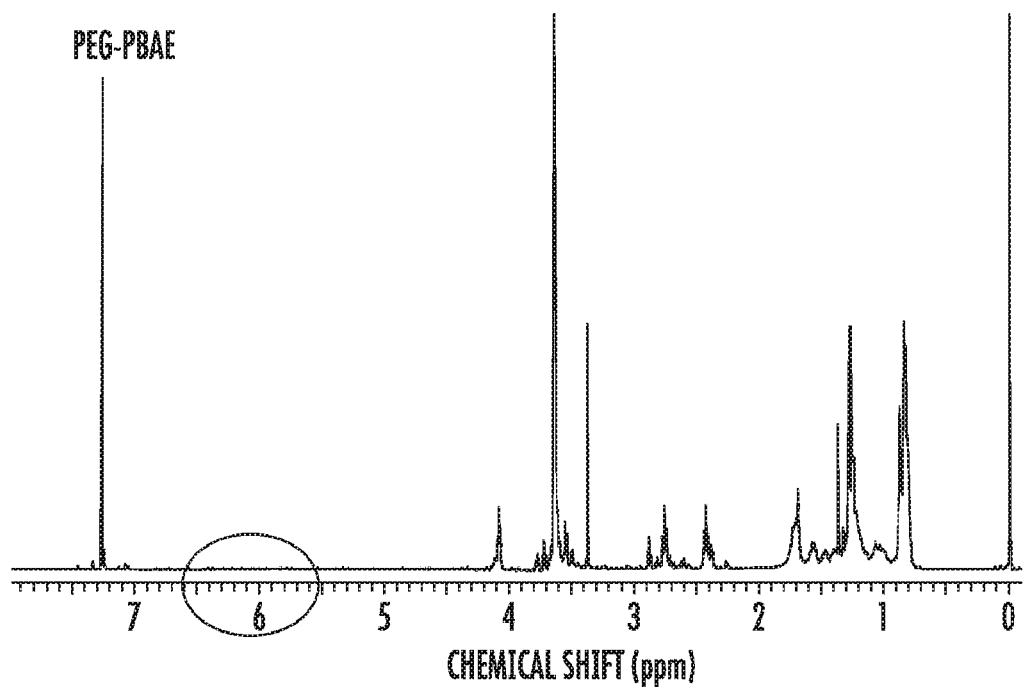
Figure 1B:
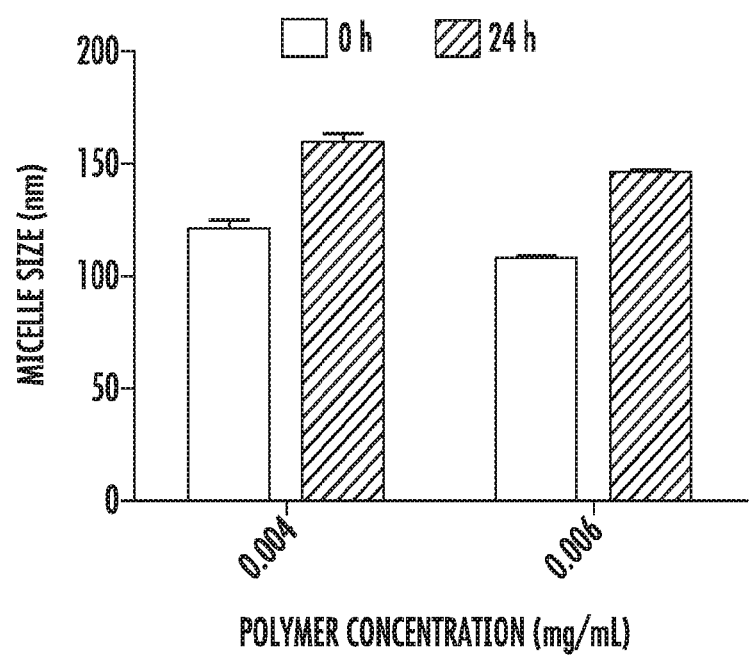
Figure 2A:
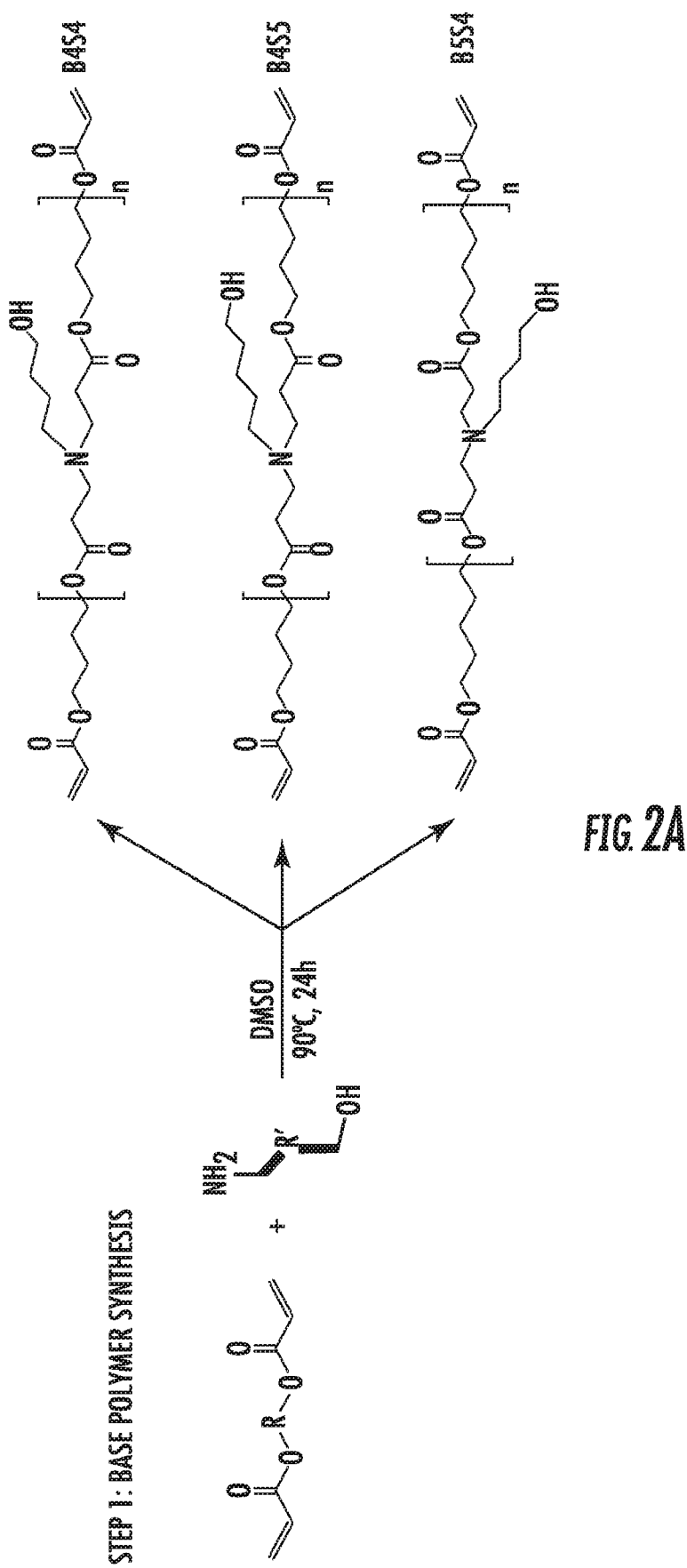
Figure 2A:
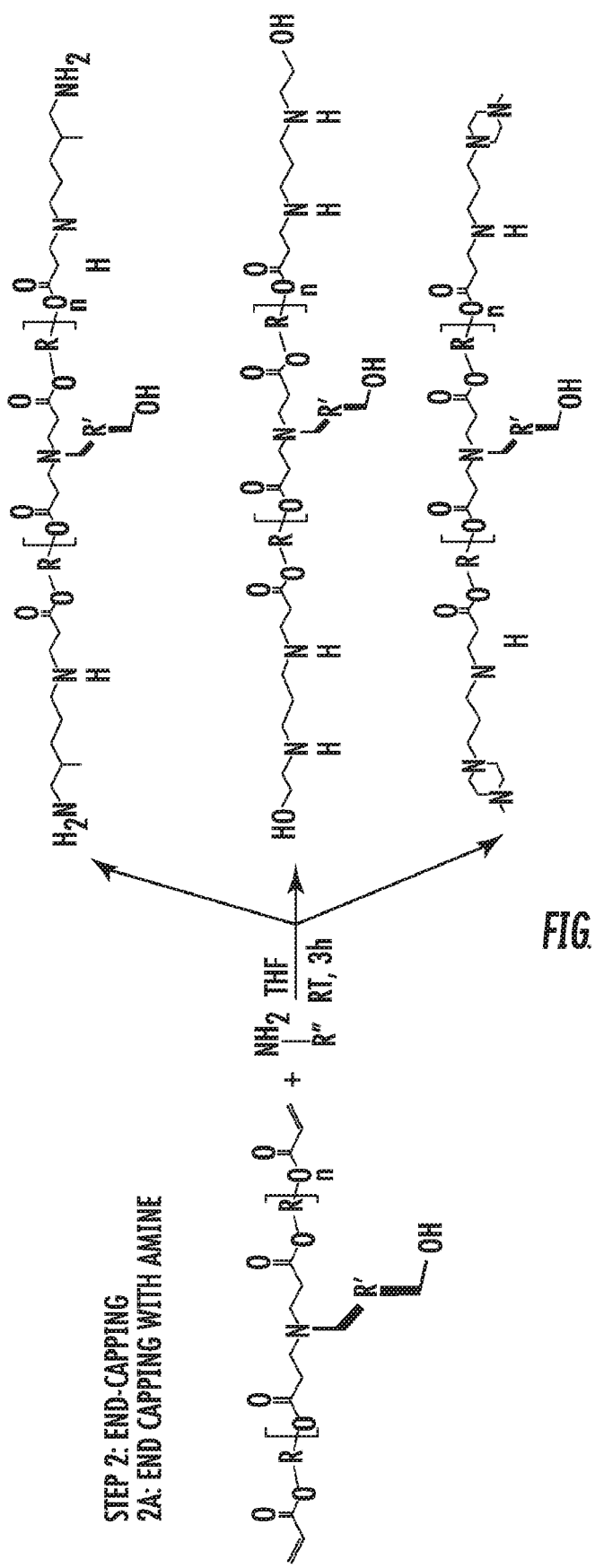
Figure 2A:
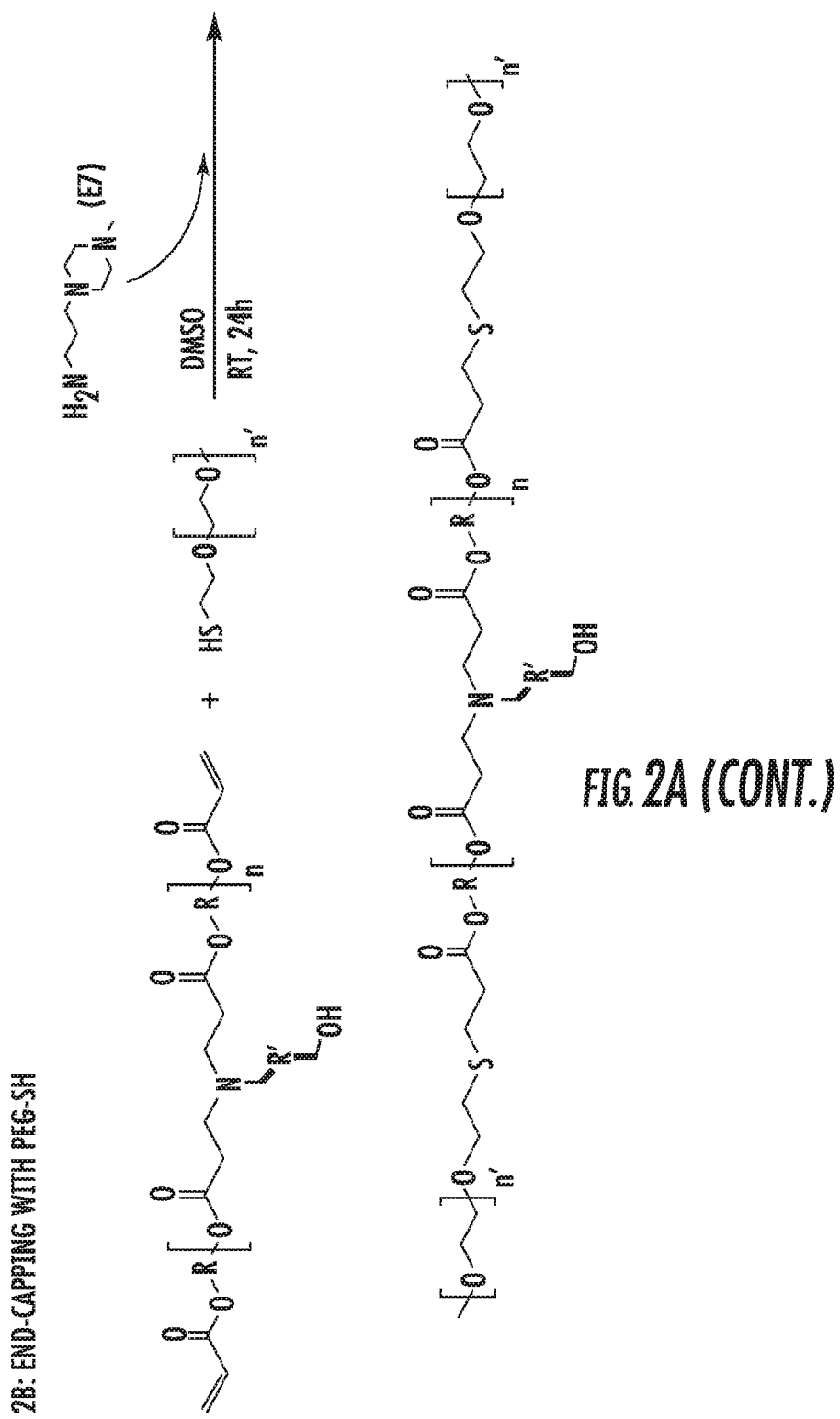
Figure 2B:
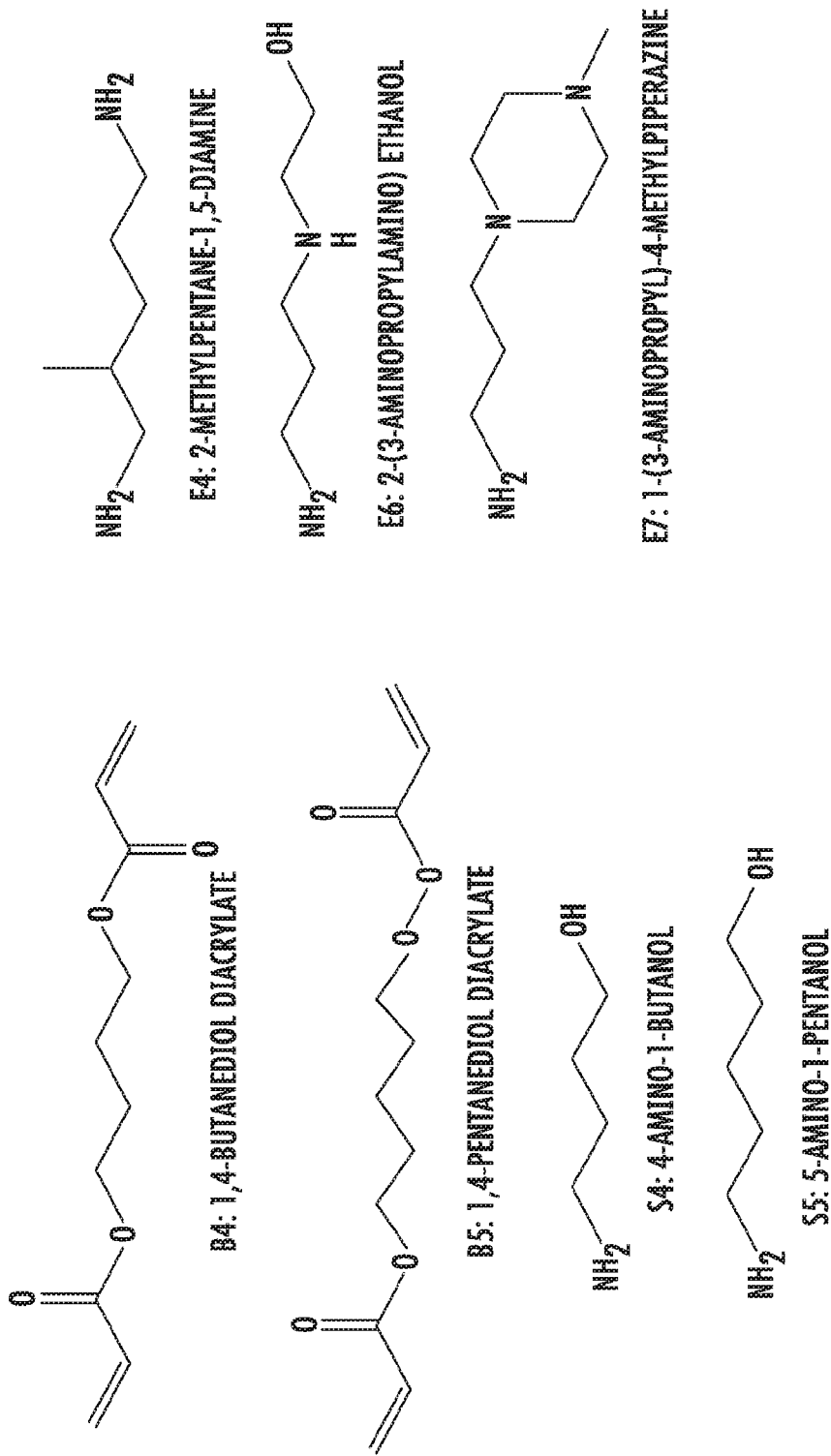
Figure 3:
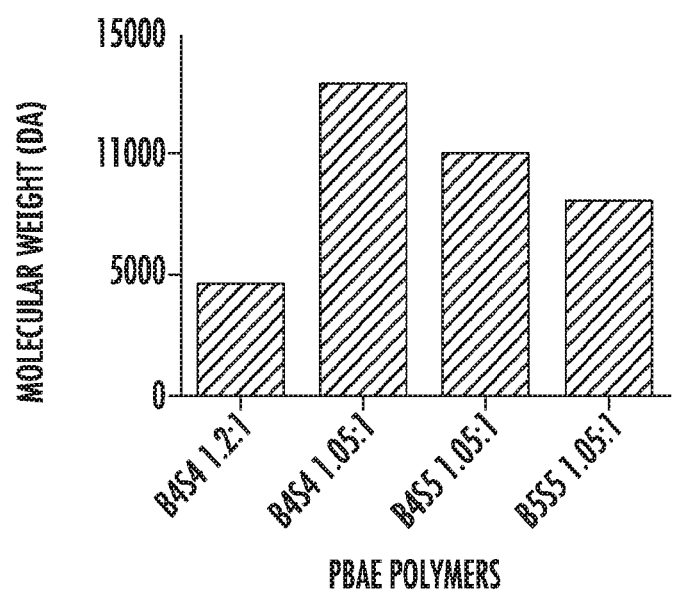
Figure 4A:
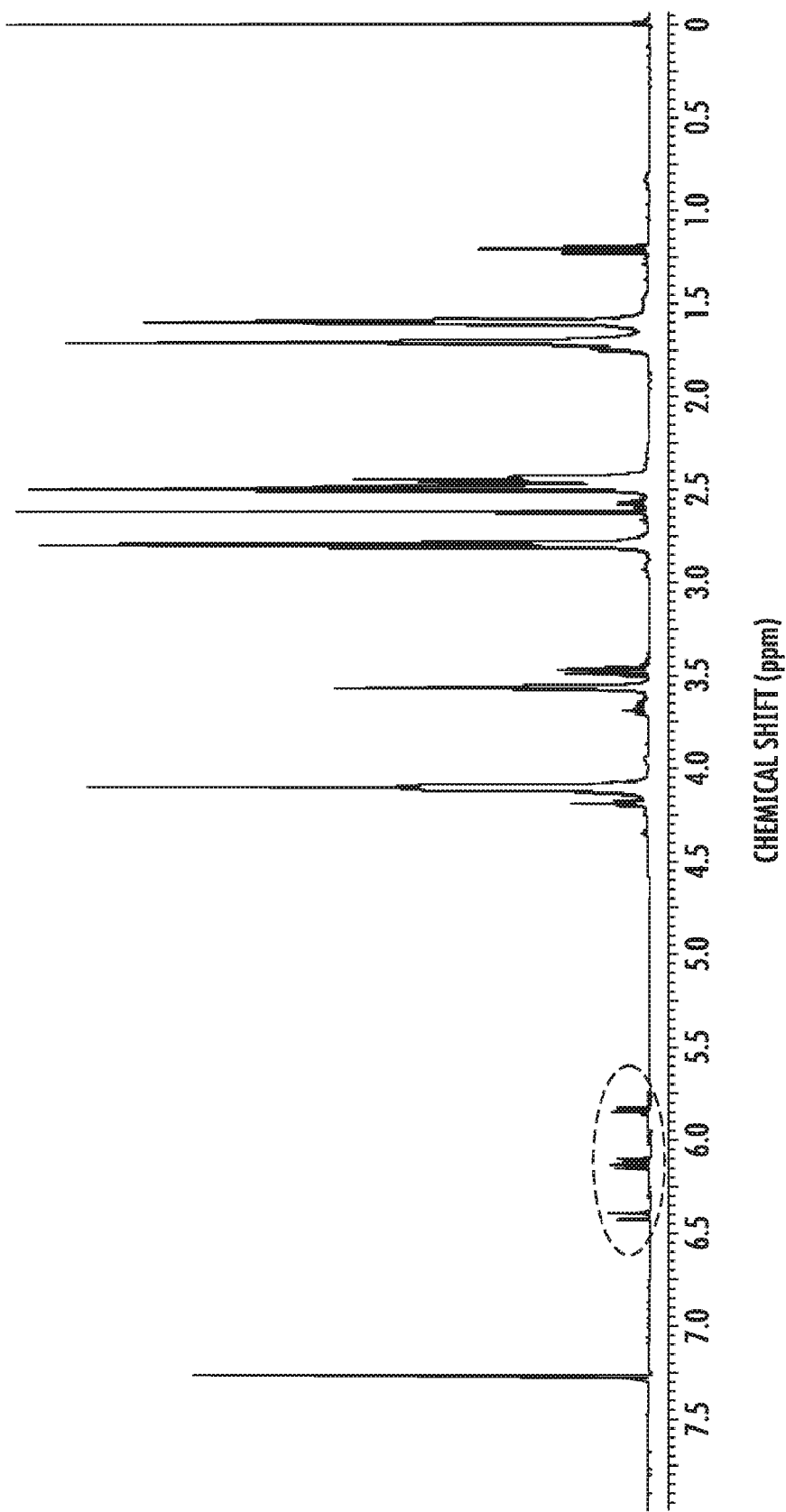
Figure 4B:
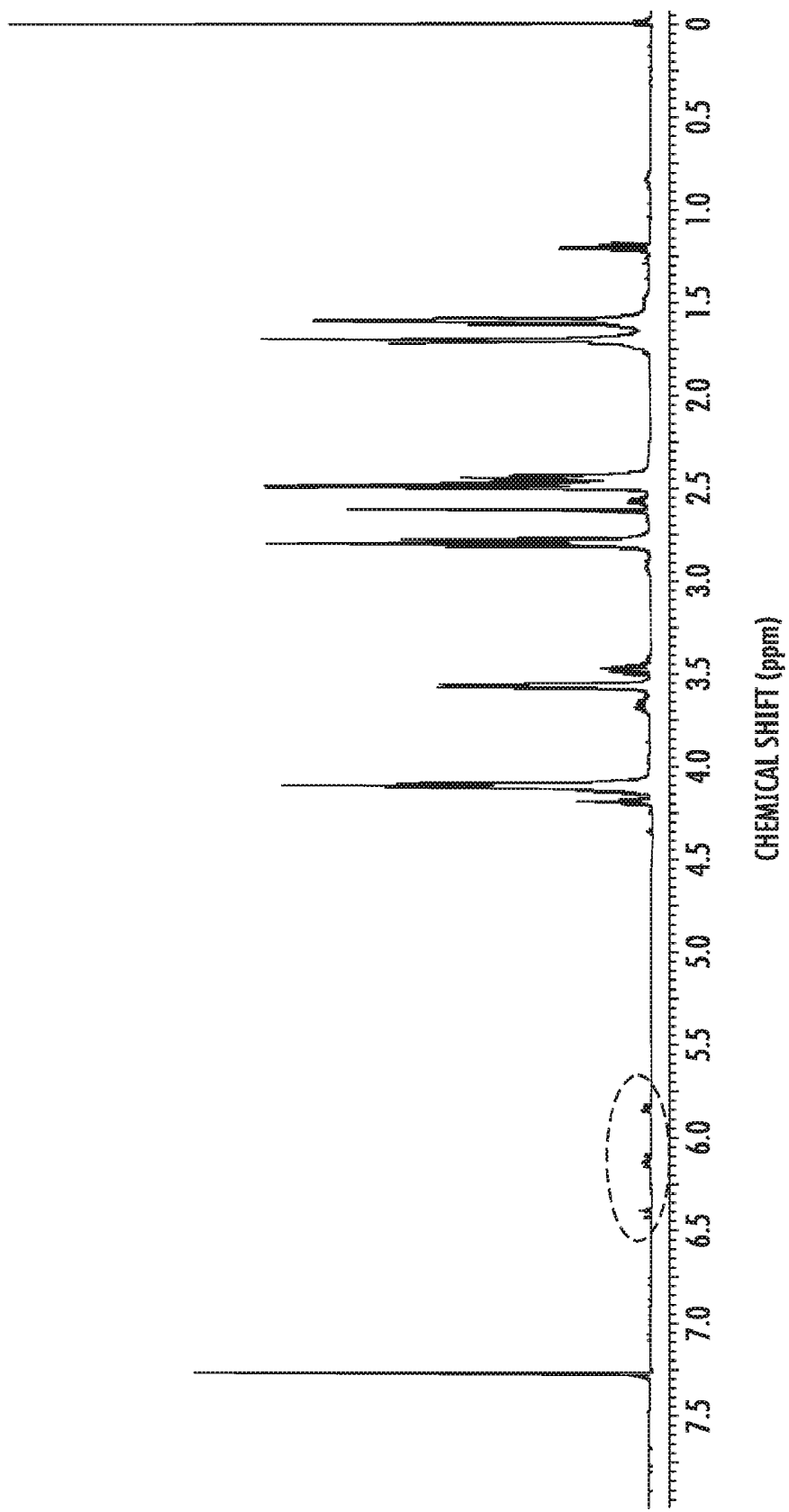
Figure 5A:
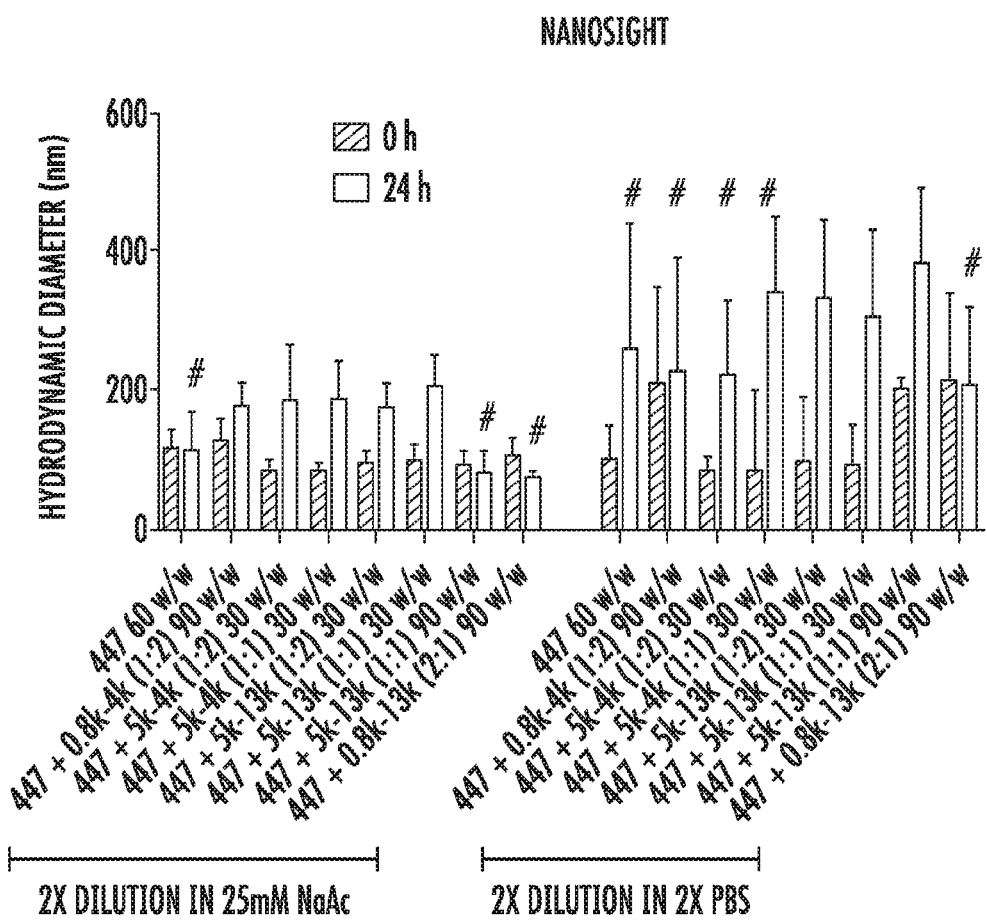
Figure 5B:
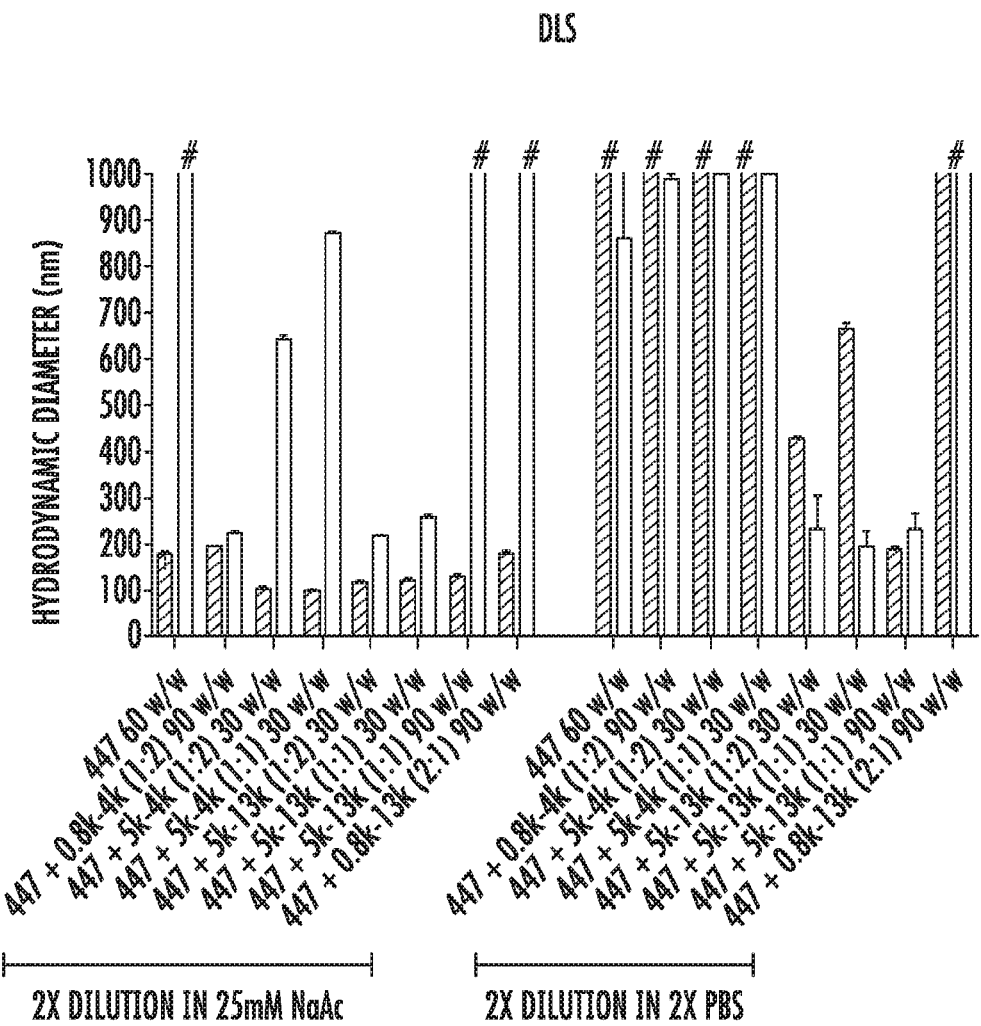
Figure 6:
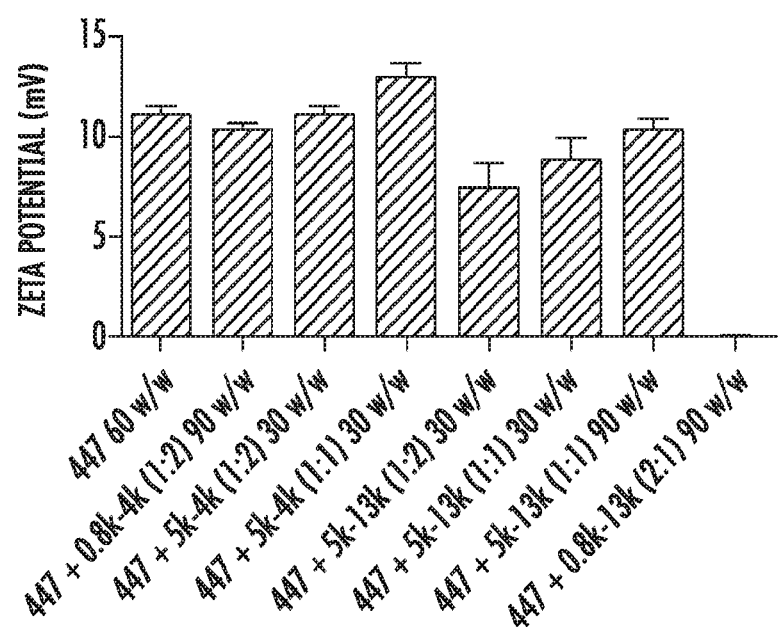
Figure 7A:
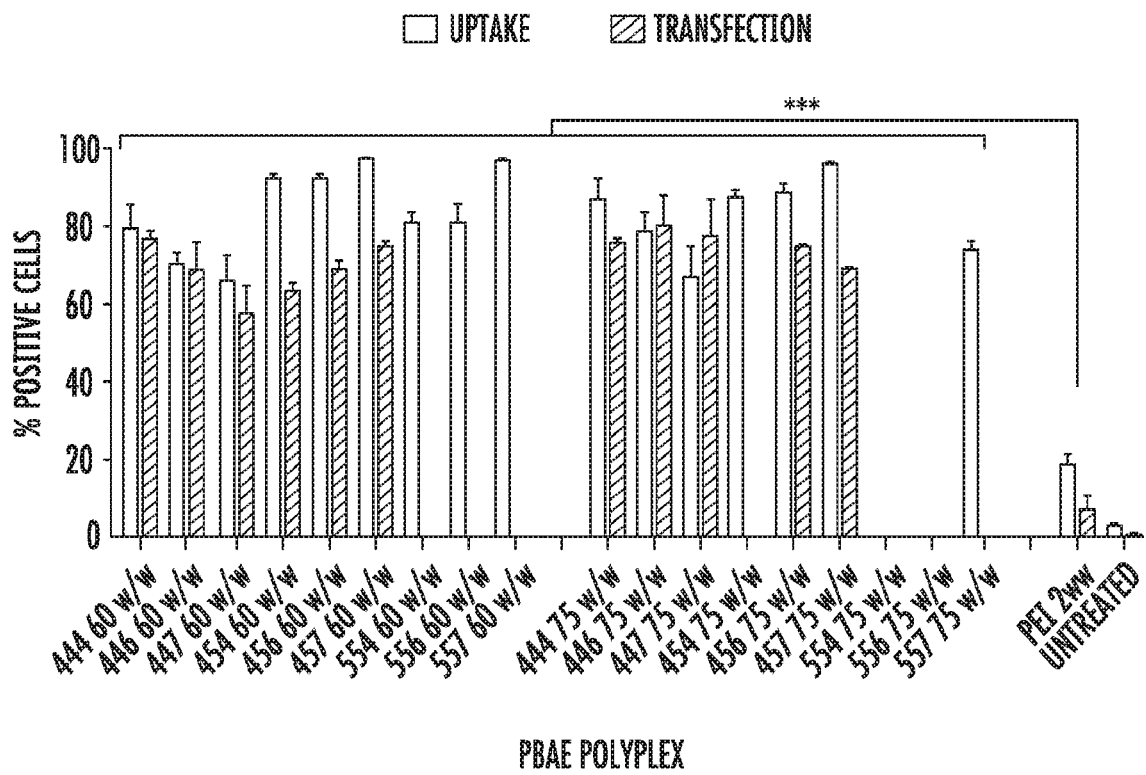
Figure 7B:
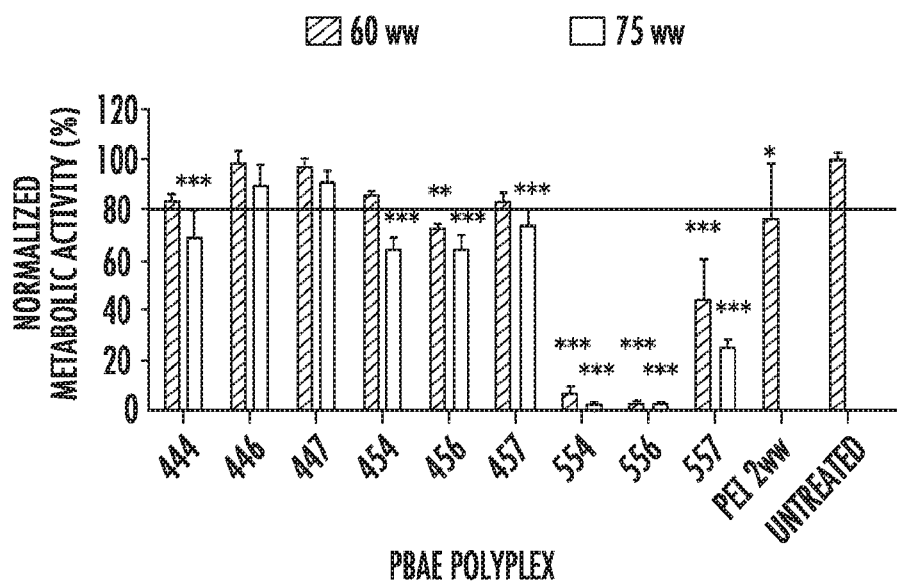
Figure 7C:
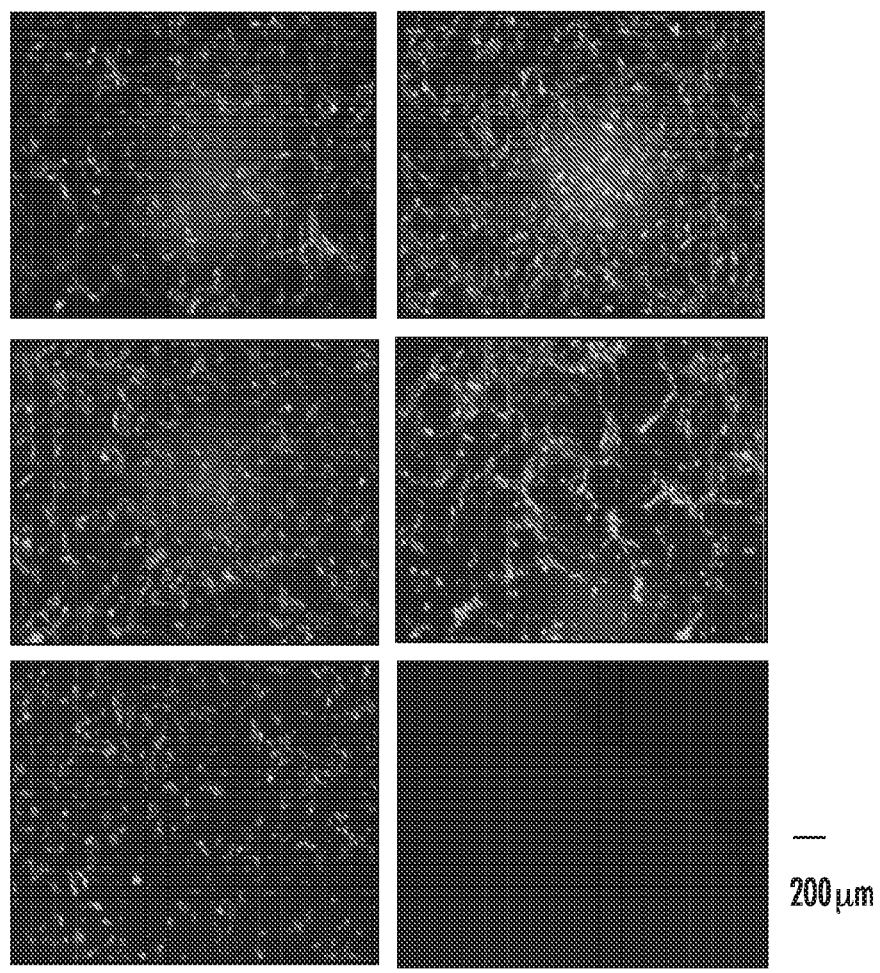
Figure 8A:
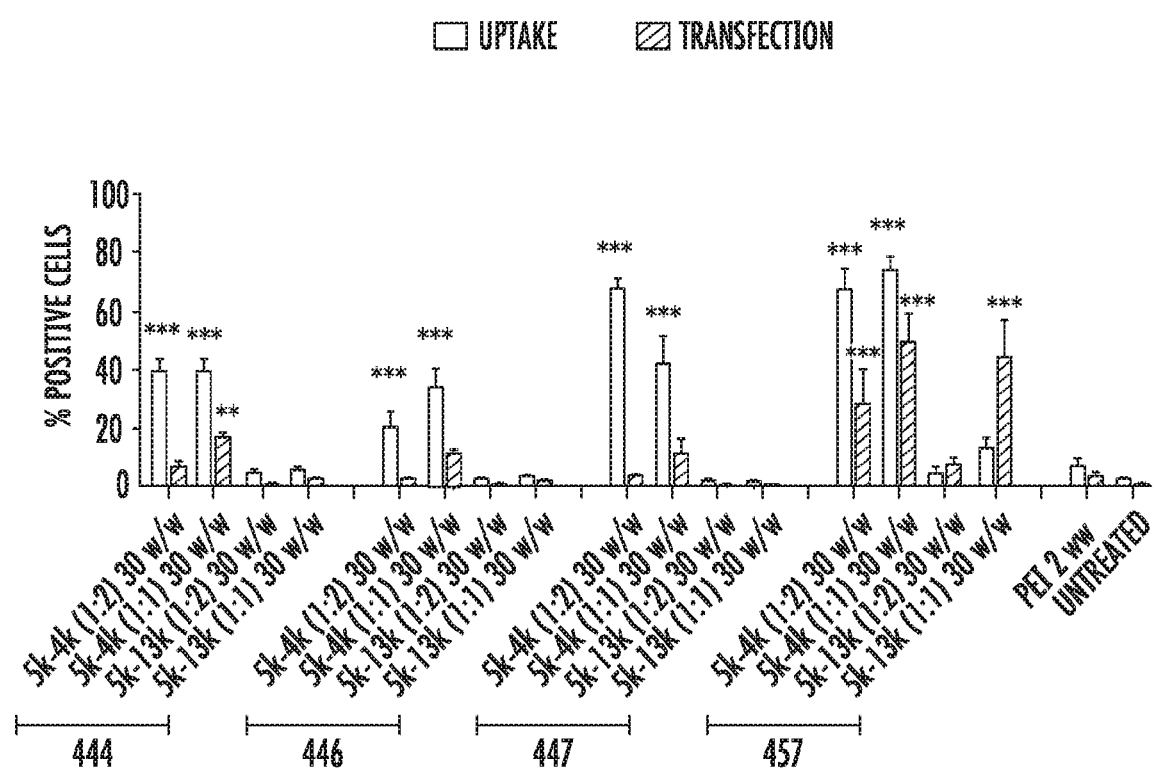
Figure 8B:
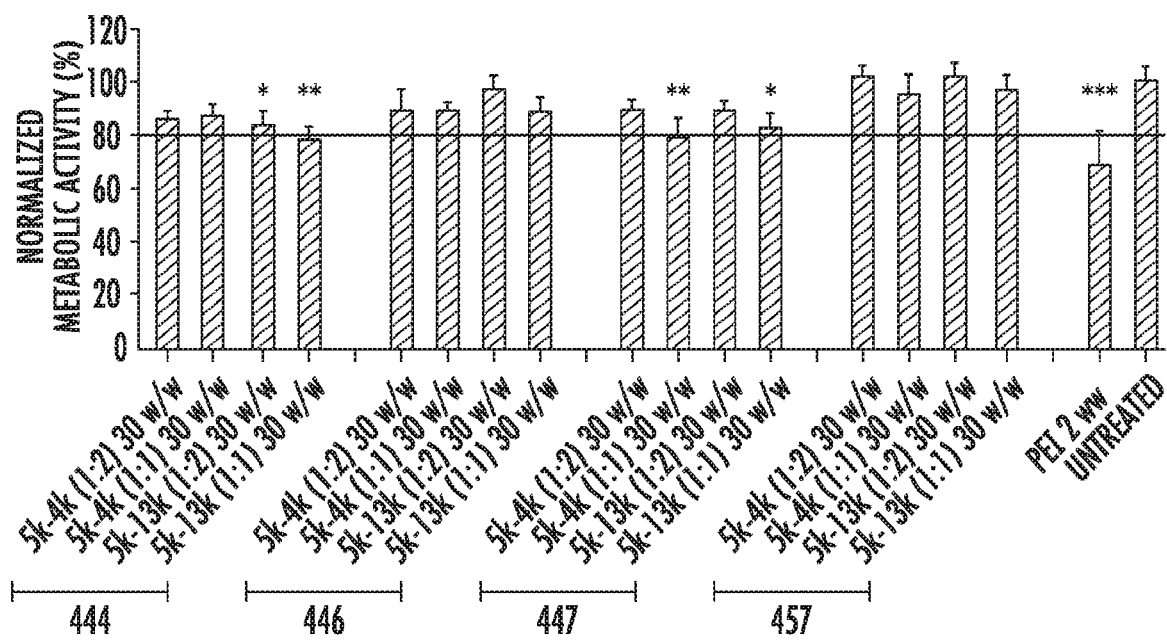
Figure 8C:
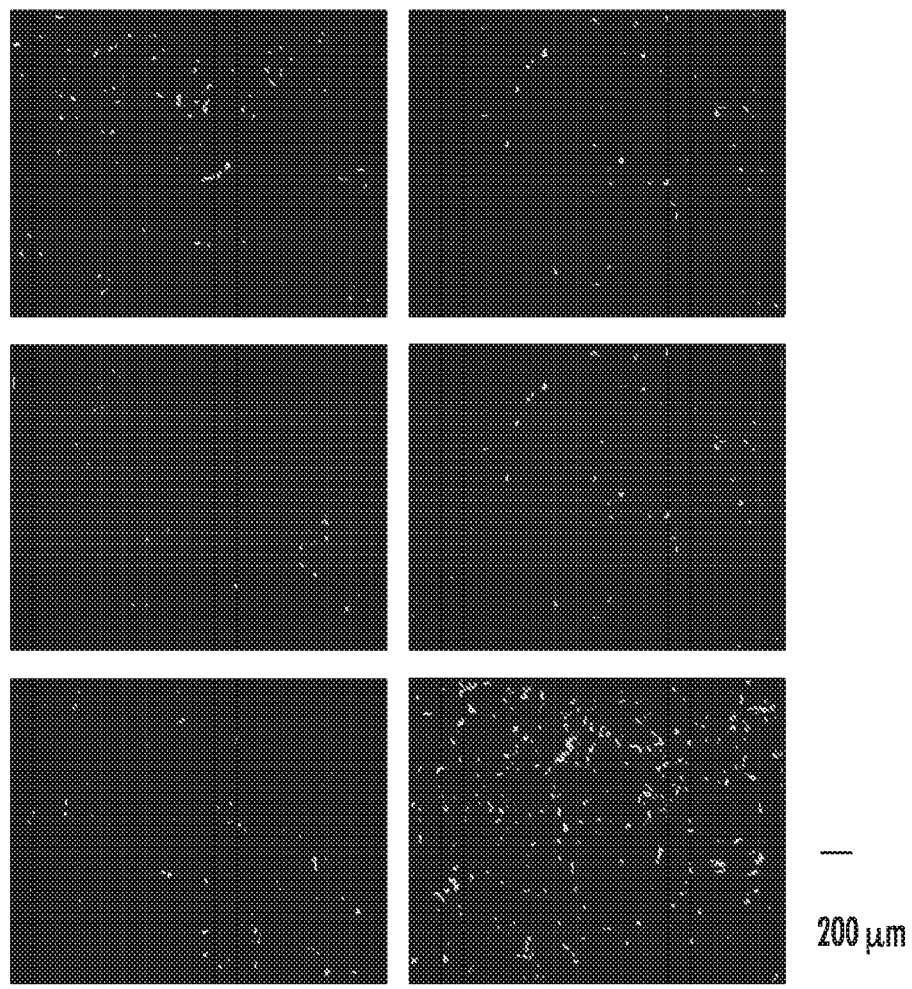
Figure 9:
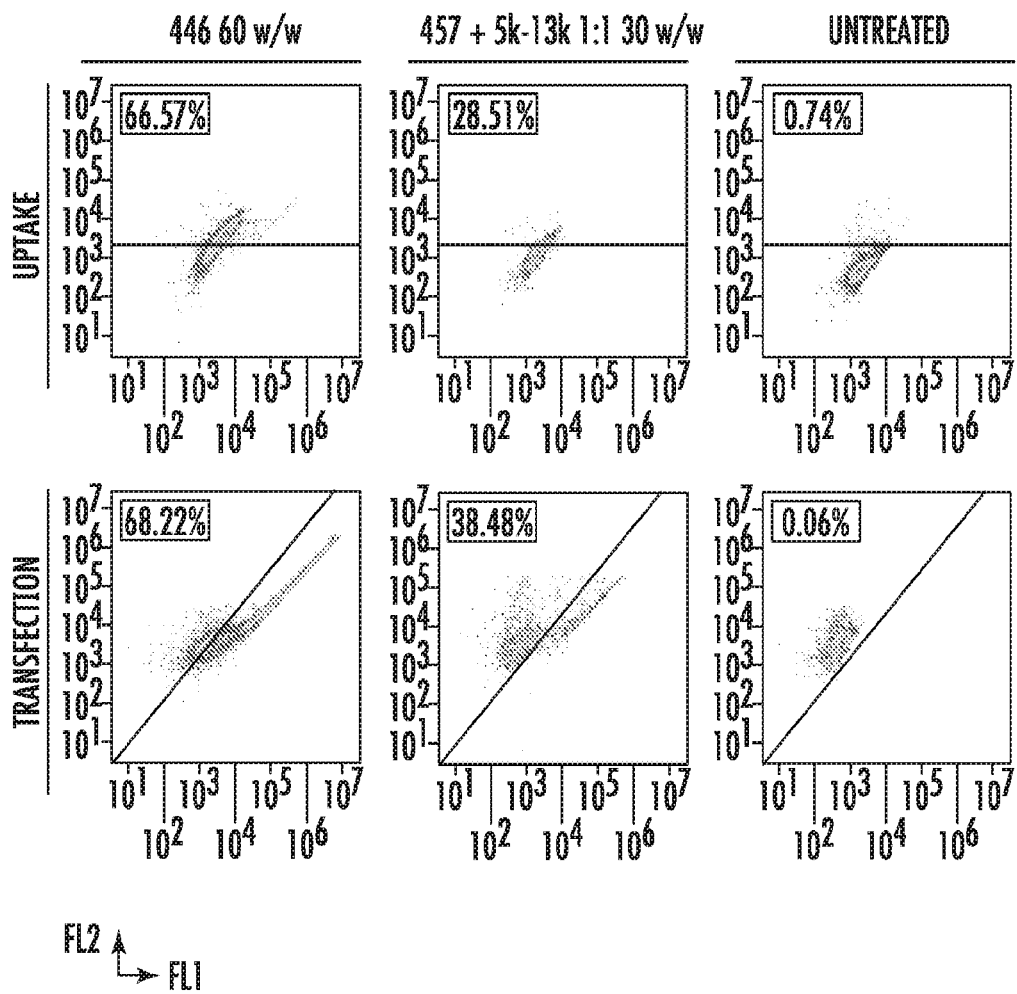
Figure 10:
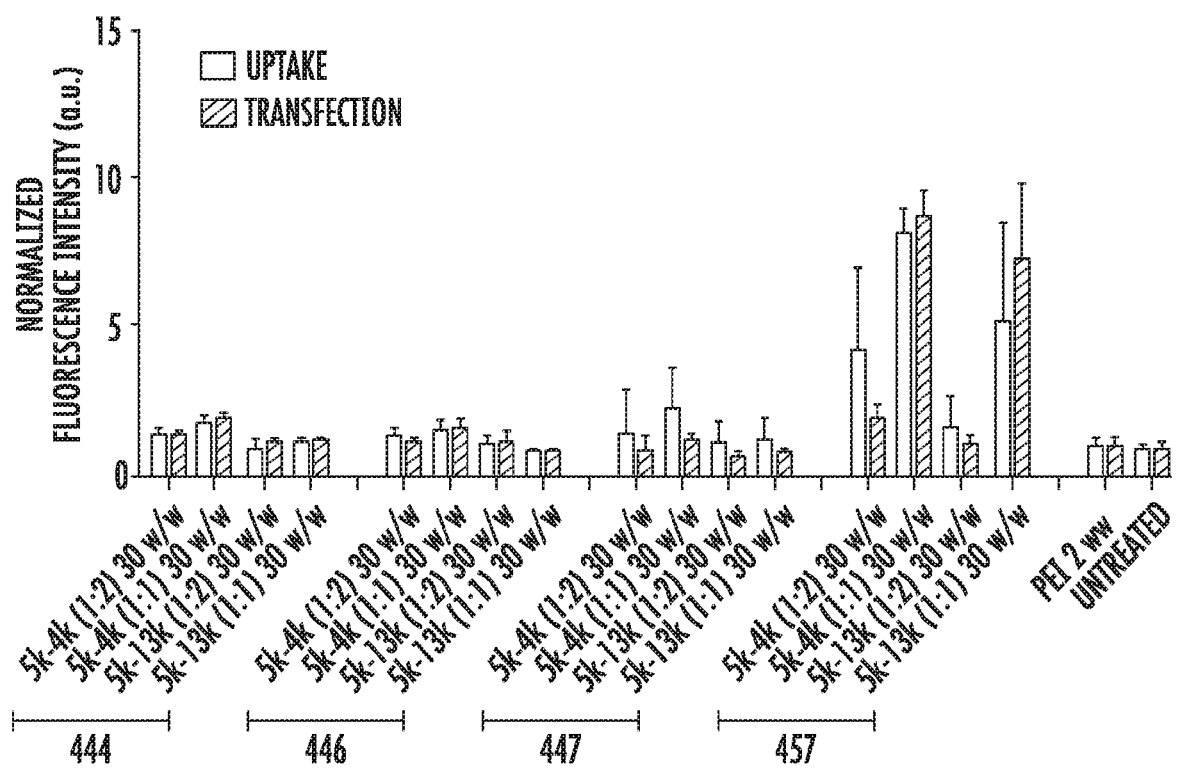
Figure 11A:
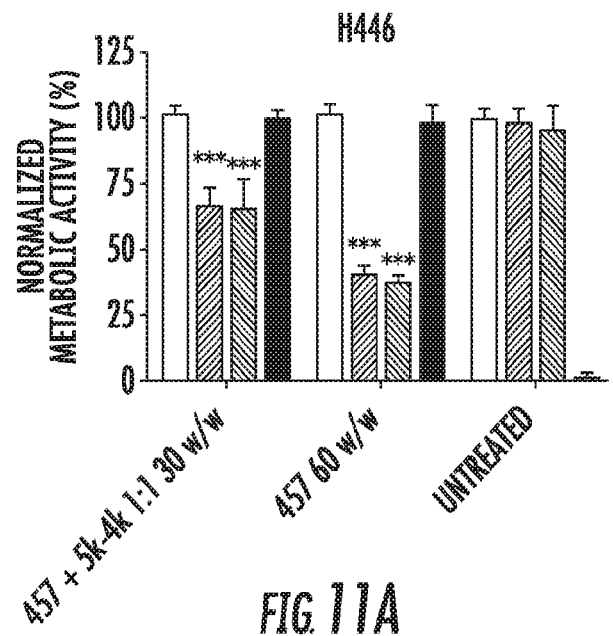
Figure 11B:
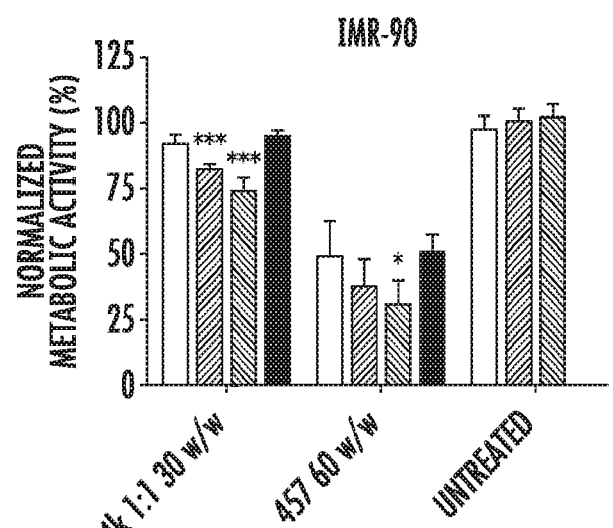
Figure 12:
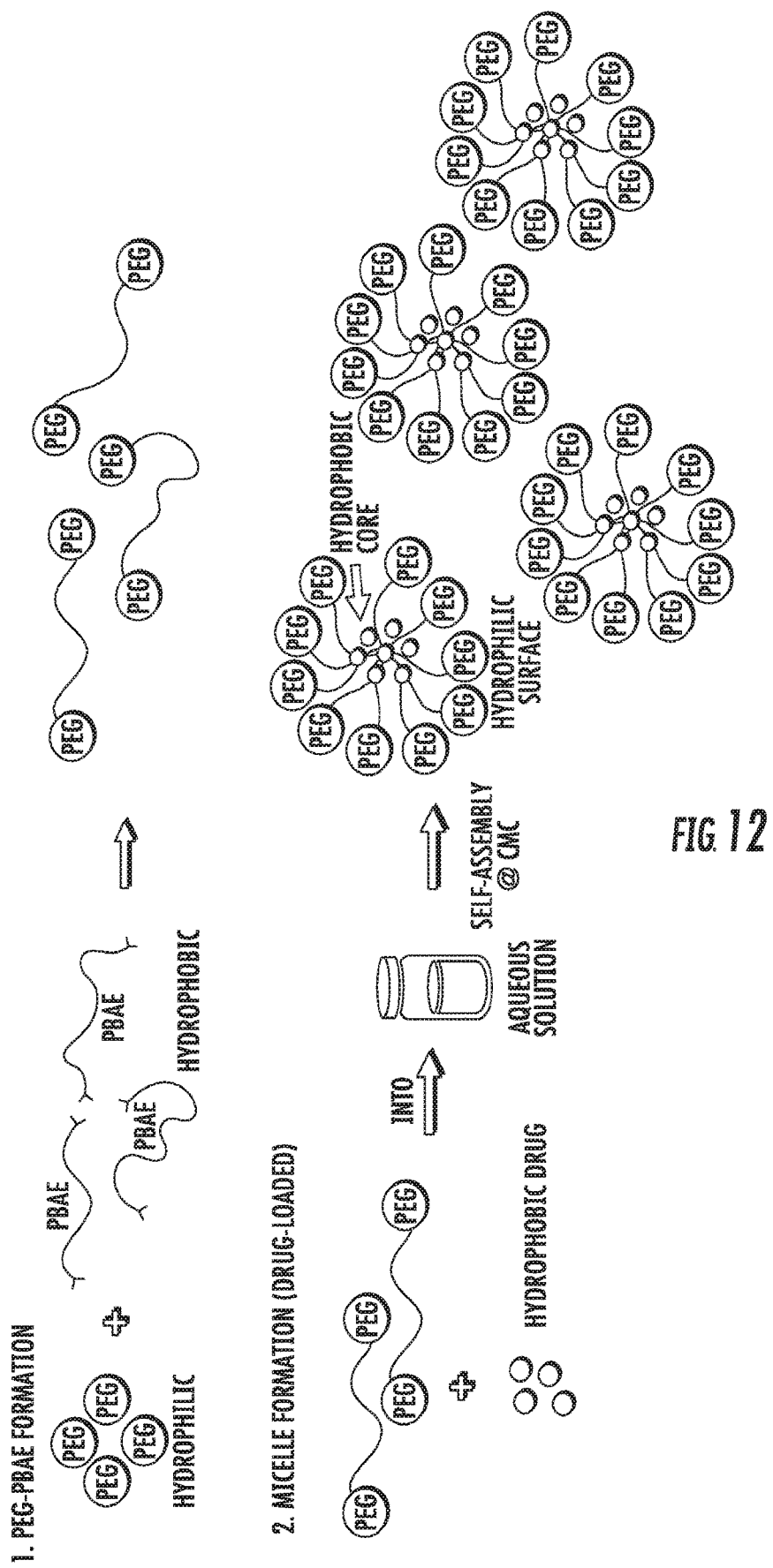
Figure 13:
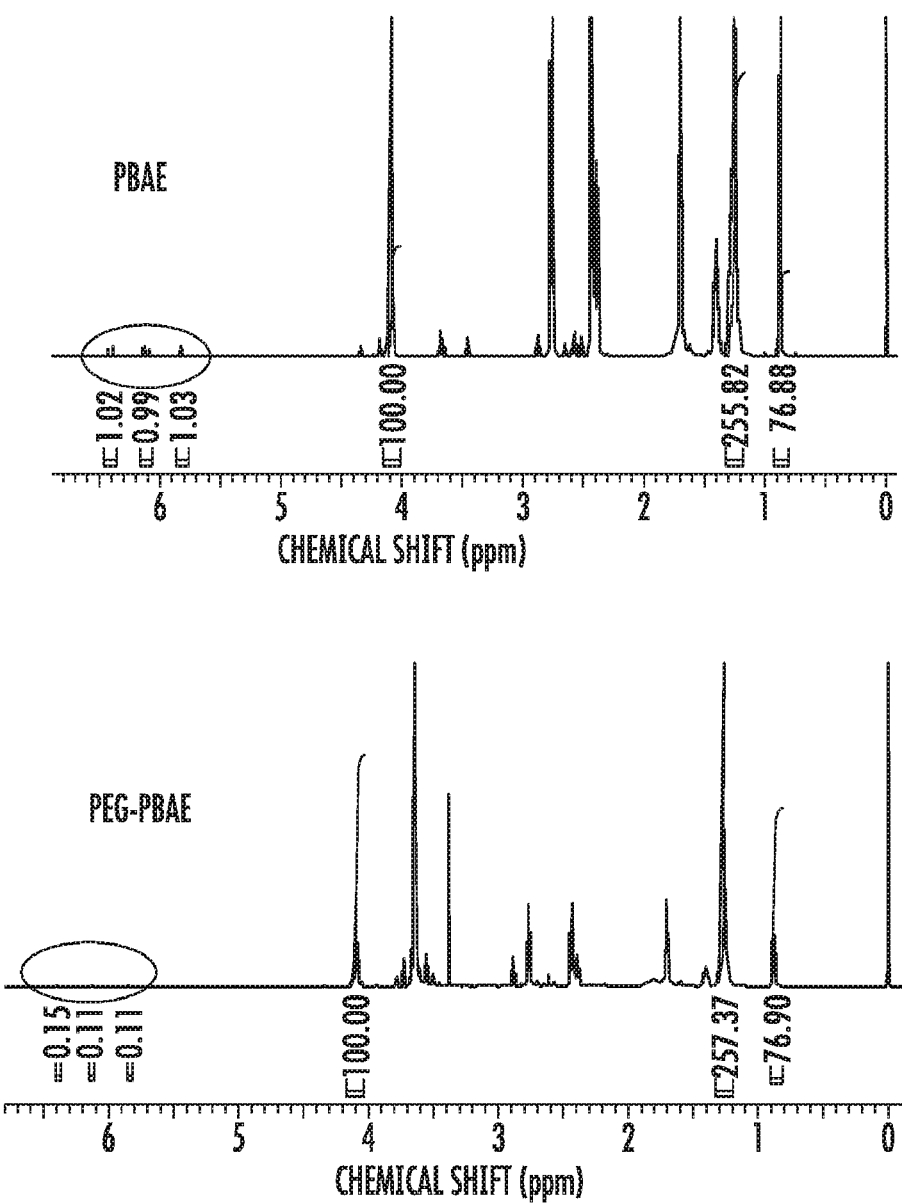
Figure 14A:
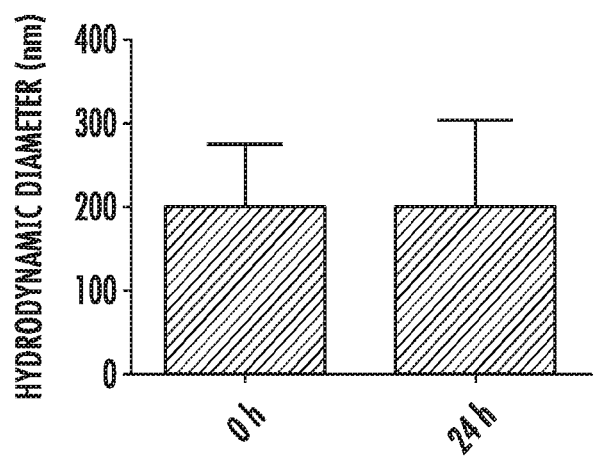
Figure 14B:
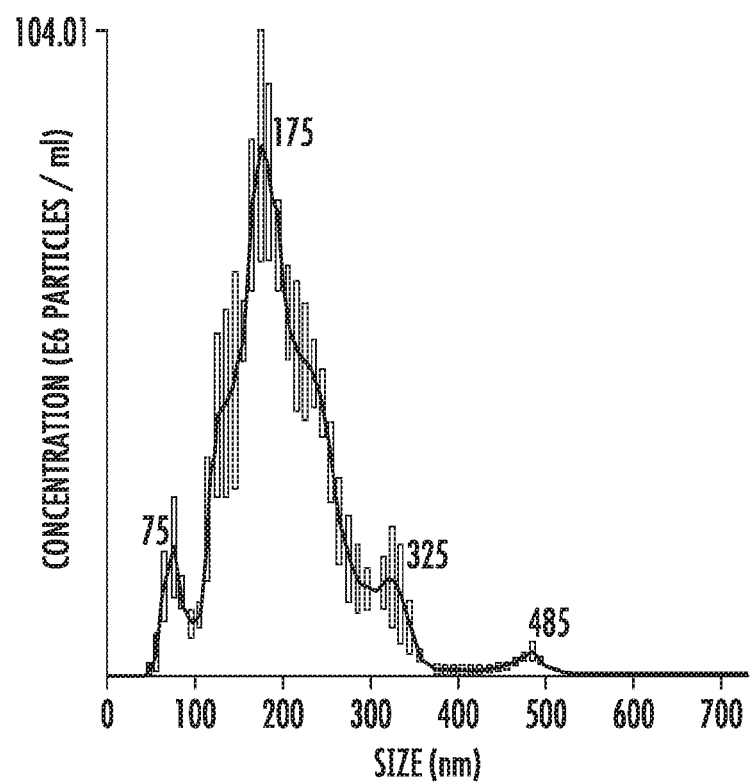
Figure 14B:
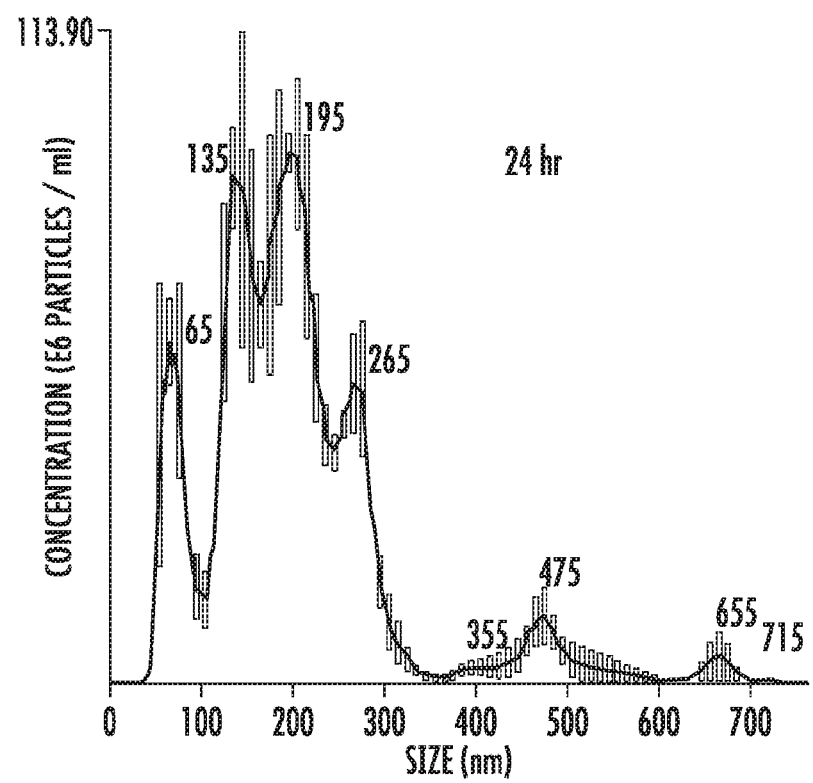
Figure 14C:
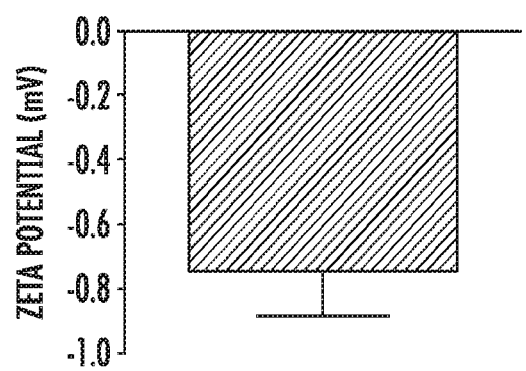
Figure 15:
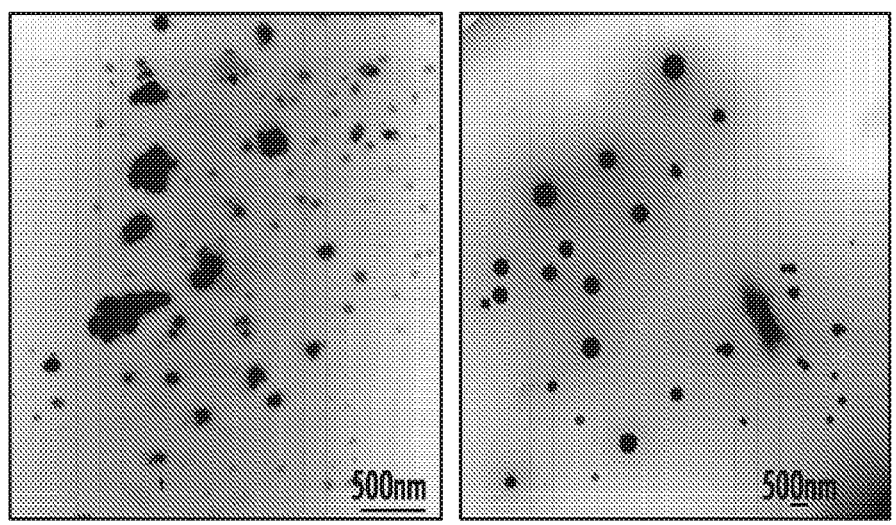
Figure 16:
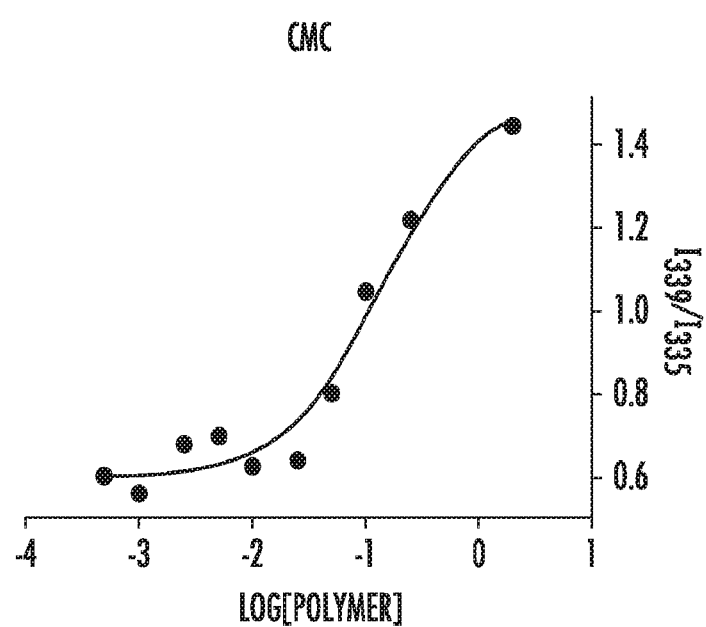

Having thus described the presently disclosed subject matter in general terms, reference will now be made to the accompanying Figures, which are not necessarily drawn to scale, and wherein:

FIG. 1A shows the $^1$H NMR spectra of a poly(ethylene glycol)-b-poly(β-amino ester) (PEG-PBAE). The absence of acrylate peaks (circled) confirms PEG conjugation to the backbone PBAE polymer;

FIG. 1B shows the micelle size of a poly(ethylene glycol)-b-poly(β-amino ester) (PEG-PBAE) at 0 hour and 24 hours in PBS as measured with Nanosight;

FIG. 2A shows a representative synthesis scheme of conventionally end-capped poly(β-amino ester)s (ePBAEs) and poly(ethylene glycol)-co-poly(β-amino ester)s (PEG-PBAEs);

FIG. 2B shows representative chemical structures of representative monomers used for the synthesis of ePBAEs and PEG-PBAEs;

FIG. 3 shows the molecular weights of four representative PBAE backbone polymers used to PEGylate or end-cap the PBAE. Ratios are molar ratios of (B) to (S) monomers used during polymer synthesis. Molecular weights are determined by taking ratios of the area under peaks of the $^1$H NMR spectra;

FIG. 4A, FIG. 4B, and FIG. 4C show $^1$H NMR spectra of (FIG. 4A) B4S4 1.2:1, (FIG. 4B) B4S4 1.05:1, (FIG. 4C) B4S4 1.2:1 end-capped with PEG$_{5k}$ to synthesize 5k-4k. The removal of acrylate peaks (shown by circles) confirms the complete conjugation of the PEG-SH molecule;

FIG. 5A and FIG. 5B show the size of representative polyplexes formed by self-assembly of enhanced green fluorescent protein (pEGFP) DNA with 447 alone or in combination with PEG-PBAE at various polymer:DNA and 447:PEG-PBAE w/w ratios. The stability of the polyplexes was tested by sizing them after 24-hour incubation in either 25-mM NaAc or PBS at room temperature. #: Indicates formulation conditions where polyplex aggregation is occurring, leading to unreliable size measurements (low particle concentration by NTA or greater than a micron in size by DLS);

FIG. 6 shows the zeta potential of the presently disclosed PEG-PBAE polyplexes. Data are mean±SD of particle population for NTA and mean±SD of three independent measurements for DLS;

FIG. 7A shows flow cytometry data indicating the uptake and transfection efficacy of nine representative PBAE polyplexes in H446 cells 4 hrs and 2 days post-transfection, respectively. The efficiency is in terms of percentage of live H446 cells positive for Cy-3 (uptake) or EGFP (transfection). Efficacy of PBAEs is compared to that of polyethylenimine (PEI) 2 w/w. Data are mean±SD (n=4) (***$p<0.001$ compared to untreated);

FIG. 7B shows the cytotoxicity of representative PBAE polyplexes, quantified by normalizing metabolic activity to untreated cells. Data are mean±SD (n=3) (*$p<0.001$, $p<0.01$, *$P<0.05$ compared to untreated);

FIG. 7C shows representative fluorescence microscope images (10×) of H446 cells transfected with four different PBAE polymers at 60 w/w and controls. Scale bar is 200 μm for all panels;

FIG. 8A shows flow cytometry data indicating the uptake and transfection efficacy of 16 different formulations of representative PEG-PBAE polyplexes in H446 cells 4 hrs and 2 days post-transfection, respectively. The efficiency is in terms of percentage of live H446 cells positive for Cy-3 (uptake) or EGFP (transfection). Data are mean±SD (n=4) (*$p<0.001$, $p<0.01$ compared to untreated);

FIG. 8B shows the cytotoxicity of representative PEG-PBAE polyplexes, quantified by normalizing metabolic activity to untreated cells. Data are mean±SD (n=3) (*$p<0.001$, $p<0.01$, *$P<0.05$ compared to untreated);

FIG. 8C shows representative fluorescence microscope images (10×) of H446 cells transfected with six different PEG-PBAE polyplex formulations;

FIG. 9 is flow cytometry plots showing the uptake and transfection efficacy of 446 60 w/w PBAE polyplexes, 457+5k-13k 1:1 30 w/w PEG-PBAE polyplexes, and untreated control in H446 cells;

FIG. 10 is flow cytometry data showing the uptake and transfection efficacy of 16 different formulations of PEG-PBAE polyplexes in H446 cells, in terms of the normalized geometric mean fluorescence intensity of Cy3 (uptake) or EGFP (transfection). Data are mean±SD (n=4);

FIG. 11A and FIG. 11B show percent killing of (A) H446 and (B) IMR-90 cells transfected with the optimized PEG-PBAE polyplex formulation (457+5k-13k 1:1 30 w/w) and PBAE polyplexes (457 60 w/w) delivering pHSV-tk, followed by two sequential ganciclovir treatments at either 10 or 20 g/mL dosage. Cell death is measured by MTS assay and normalized to metabolic activity of untreated cells. Data are mean±SD (n=4) (*$p<0.05$, ***$p<0.001$ compared to pEGFp control of each group);

FIG. 12 shows a representative schematic of PEG-PBAE copolymer micelle self-assembly in aqueous solution with hydrophobic drug encapsulated;

FIG. 13 shows NMR analysis confirming PEG conjugation to both ends of PBAE base polymer by the absence of acrylate peaks;

FIG. 14A, FIG. 14B, and FIG. 14C show particle characterization: (FIG. 14A) 0 hr and 24 hr sizing of particles (nm); (FIG. 14B) histogram of particle concentration vs. size at 0 hr and 24 hr using Nanosight; and (FIG. 14C) zeta potential (mV) of particles determined using DLS;

FIG. 15 shows representative TEM images. PEG-PBAE micelles prepared at 0.1 mg/mL with uranyl acetate staining; and FIG. 16 shows critical micelle concentration: a plot showing the change in $I_{339}/I_{335}$ for pyrene as the concentration (mg/mL) for PEG-PBAE is increased. The critical micelle concentration is the concentration of polymers at which above will form micelles.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Poly(β-Amino Ester)-Co-Polyethylene Glycol (PEG-PBAE-PEG)Co-Polymers

Challenges in developing compositions for delivering therapeutic cargo to specific targets, such as a cancer cell, include improving the efficacy of the particles in vivo, reducing non-specific clearance in the blood, and minimizing adsorption of protein molecules to the particles. The presently disclosed polymer compositions address these challenges and more.

The presently disclosed subject matter provides polyethylene glycol (PEG)-poly(β-amino ester) (PBAE) co-polymers, referred to herein as "PEGylated PBAE," which can be prepared through a novel synthesis scheme. DNA, siRNA, and other cargos can associate with a blend of PEGylated PBAE and unmodified PBAE to form stable particles for drug and gene delivery. For example, in some embodiments, the presently disclosed compounds are useful for delivering a therapeutic agent to a cell, a specific cell line, a tissue, or an organism. The therapeutic agent can include a gene, DNA, RNA, siRNA, miRNA, isRNA, agRNA, smRNA, a nucleic acid, a peptide, a protein, a chemotherapeutic agent, a hydrophobic drug, and a small molecule drug. Further, PEGylated PBAE, an amphiphilic polymer, also forms micelles that can deliver hydrophobic drugs.

In some embodiments, the presently disclosed subject matter provides a polyethylene glycol (PEG)-b-poly(β-amino ester) (PBAE) co-polymer (PEG-PBAE) of Formula (I):

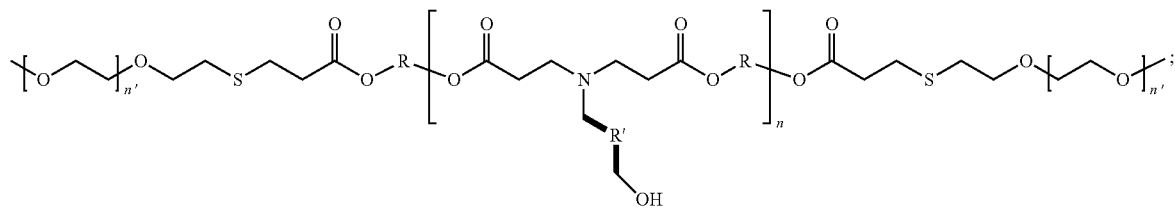

wherein: each n and n' is independently an integer from 1 to 10,000, 1 to 1,000, 1 to 100, 1 to 30, 5 to 20, 10 to 15, and 1 to 10; R is $C_2$ to $C_8$ substituted or unsubstituted linear or branched alkylene, including $C_2$, $C_3$, $C_4$, $C_5$, $C_6$, $C_7$, and $C_8$; R' is $C_1$ to $C_5$ substituted or unsubstituted linear or branched alkylene, including $C_1$, $C_2$, $C_3$, $C_4$, and $C_5$, wherein each R and R' can independently be the same or different; and pharmaceutically acceptable salts thereof. In some embodiments, R is further substituted by 0-4 alkyl groups, e.g., methyl group and as alkyl is defined further herein below, along the alkylene chain.

The side chain comprising R' can include any group that facilitates solubility in water and/or hydrogen bonding, for example, OH, $NH_2$ and SH.

In some embodiments, the compound of Formula (I) further comprises a counter ion selected from the group consisting of chloride, fluoride, bromide, iodide, sulfate, nitrate, fumarate, acetate, carbonate, stearate, laurate, and oleate.

In some embodiments, the PBAE backbone "B" is selected from the group consisting of:

(B3)

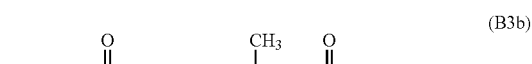
(B3b)

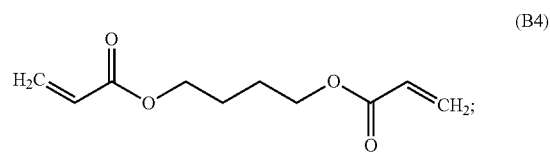
(B4)

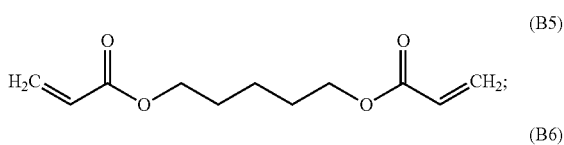
(B5)

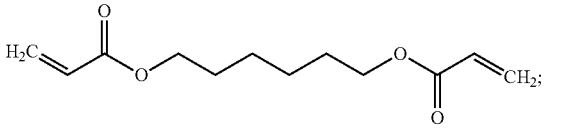
(B6)

-continued

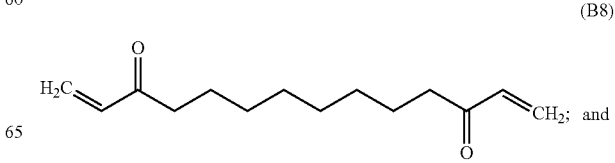
(B8) and

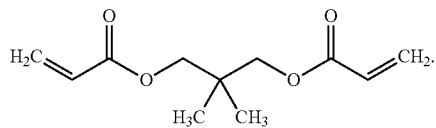
(BP2)

In some embodiments, the PBAE sidechain "S" is selected from the group consisting of:

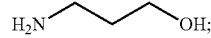
(S3)

(S4)

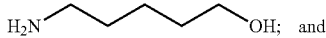
(S5)

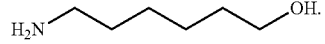
(S6)

The presently disclosed subject matter is not limited to the representative monomers disclosed herein, but also includes other structures that one skilled in the art could use to create similar degrading cationic polymers. Suitable degrading cationic polymers are disclosed, for example, in international PCT patent application publication no. WO/2010/132879 for MULTICOMPONENT DEGRADABLE CATIONIC POLYMERS, to Green et al., published Nov. 18, 2010, international PCT patent application publication no. WO/2014/066811 for BIOREDUCIBLE POLY(beta-AMINO ESTER)S FOR SIRNA DELIVERY, to Green et al., published May 1, 2014, and U.S. patent application publication no. 2012/0114759 for PEPTIDE/PARTICLE DELIVERY SYSTEMS, to Green et al., published May 10, 2012, each of which is incorporated herein by reference in its entirety.

In some embodiments of the PEG-PBAE co-polymer of Formula (I), the PEG subunit has a molecular weight selected from the group consisting of about 0.5 kDa to about 5 kDa, about 5 kDa to about 10 kDa, about 10 kDa to about 20 kDa, and about 20 kDa to about 30 kDa. Also, in some embodiments, the PBAE subunit has a molecular weight ranging from about 1 kDa to about 5 kDa, 5 kDa to about 10 kDa, about 4 kDa to about 13 kDa, about 10 kDa to about 15 kDa, about 15 kDa to about 25 kDa, about 25 kDa to about 50 kDa, and about 50 kDa to about 100 kDa.

In particular embodiments, the PEG-PBAE co-polymer is selected from the group consisting of: $PEG_{0.8k}$-$B4S4_{4k}$-$PEG_{0.8k}$, $PEG_{0.8k}$-$B4S4_{13k}$-$PEG_{0.8k}$, $PEG_{5k}$-$B4S4_{4k}$-$PEG_{5k}$, and $PEG_{5k}$-$B4S4_{13k}$-$PEG_{5k}$.

In some embodiments, the presently disclosed subject matter provides a micelle comprising a polyethylene glycol (PEG)-b-poly(β-amino ester) (PBAE) co-polymer of Formula (I). In some embodiments, the micelle comprises a cargo. In particular embodiments, the cargo comprises one or more hydrophobic drugs.

In further embodiments, the presently disclosed subject matter provides a particle comprising a blend of a polyethylene glycol (PEG)-b-poly(β-amino ester) (PBAE) co-polymer of Formula (I) and a poly(β-amino ester) (PBAE). In particular embodiments, the poly(β-amino ester) (PBAE) comprises an unmodified poly(β-amino ester) (PBAE). In some embodiments, the particle comprises a cargo. In particular embodiments, the cargo comprises a drug or a gene. In yet more particular, the cargo comprises DNA or siRNA. Accordingly, the presently disclosed PEG-PBAE co-polymers can be used to deliver a pharmaceutical or therapeutic agent to a target, as provided herein below.

II. Poly(β-Amino Ester)-Co-Polyethylene Glycol (PEG-PBAE-PEG) Polymers for Gene and Drug Delivery In particular embodiments, the presently disclosed subject matter provides for the synthesis of a PEG-PBAE-PEG block copolymer and specific structural compositions. More particularly, the presently disclosed subject matter provides controllable and simplified 2-step reaction to synthesize PEG-PBAE-PEG. Only a specific set of reaction conditions yielded the product.

Accordingly, in some embodiments, the presently disclosed subject matter provides a method for preparing a polyethylene glycol (PEG)-b-poly(β-amino ester) (PBAE) co-polymer of Formula (I):

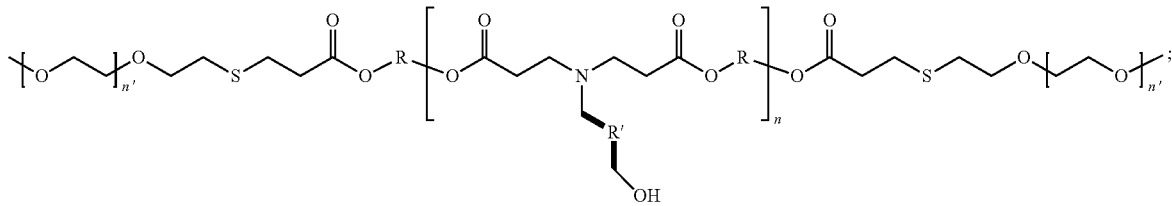

wherein: each n and n' is independently an integer from 1 to 10,000, 1 to 1,000, 1 to 100, 1 to 30, 5 to 20, 10 to 15, and 1 to 10; R is $C_2$ to $C_8$ substituted or unsubstituted linear or branched alkylene; and R' is $C_1$ to $C_5$ substituted or unsubstituted linear or branched alkylene, wherein each R and R' can independently be the same or different; and pharmaceutically acceptable salts thereof, the method comprising:

(a) synthesizing an acrylate-terminated poly(β-amino ester) (PBAE) via Michael addition of a diacrylate monomer and a primary amine-containing monomer at a molar ratio; and (b) reacting the acrylate-terminated PBAE with a functionalized PEG molecule to form a polyethylene glycol (PEG)-b-poly(β-amino ester) (PBAE) co-polymer.

In some embodiments, the diacrylate monomer comprises:

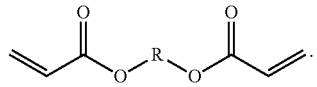

In some embodiments, the primary amine-containing monomer comprises:

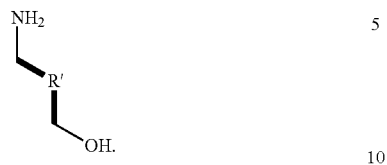

5

In some embodiments, the acrylate-terminated poly(β-amino ester) (PBAE) is selected from the group consisting of:

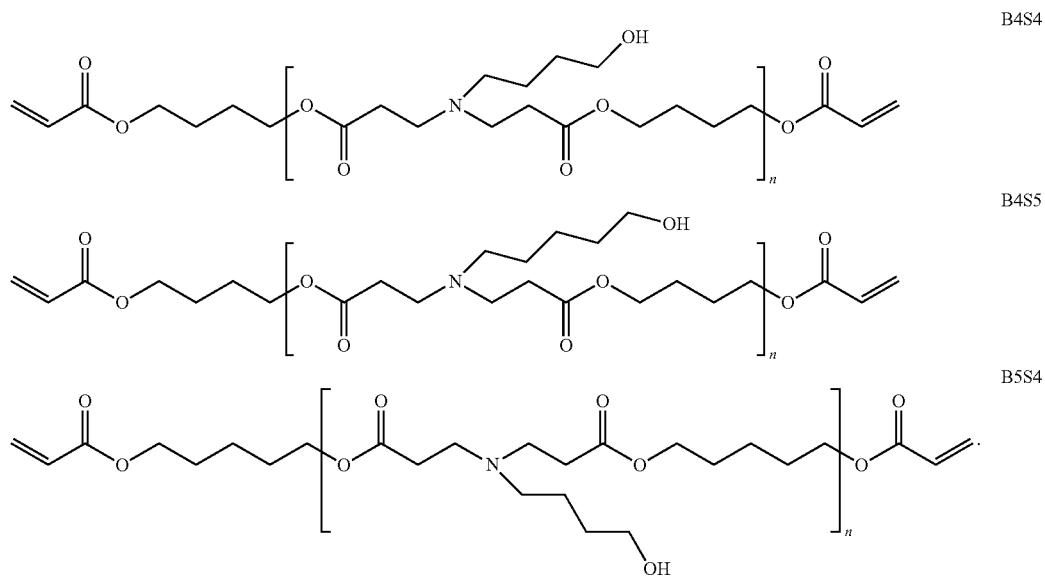

B4S4

B4S5

B5S4

In particular embodiments, the functionalized PEG molecule comprises PEG-SH.15. In some embodiments, step (b) further comprises a catalyst. In particular embodiments, the catalyst comprises 1-(3-aminopropyl)-4-methyl-piperazine.

In particular embodiments, the PBAE acrylate-terminated poly(β-amino ester) (PBAE) synthesized in step (a) is end-capped with an amine-containing small molecule to yield an unmodified PBAE.

In representative embodiments, the unmodified PBAE is selected from the group consisting of:

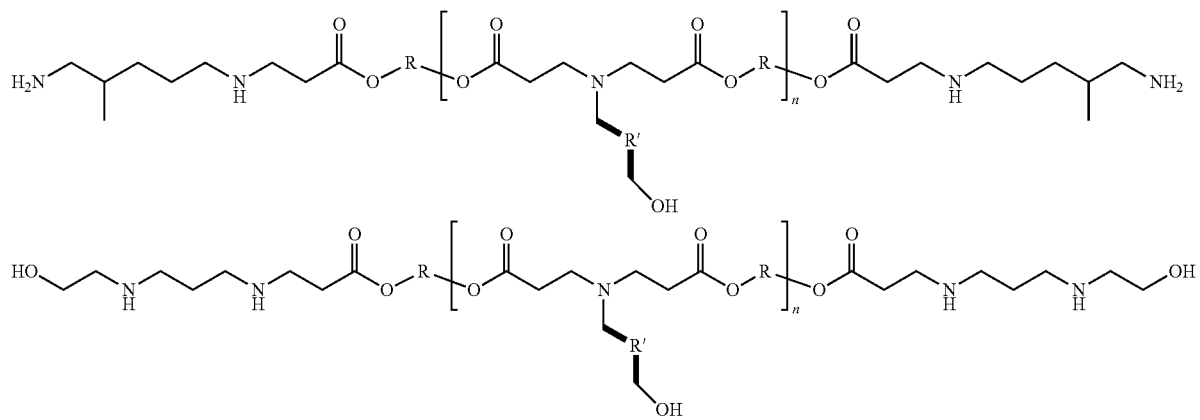

-continued

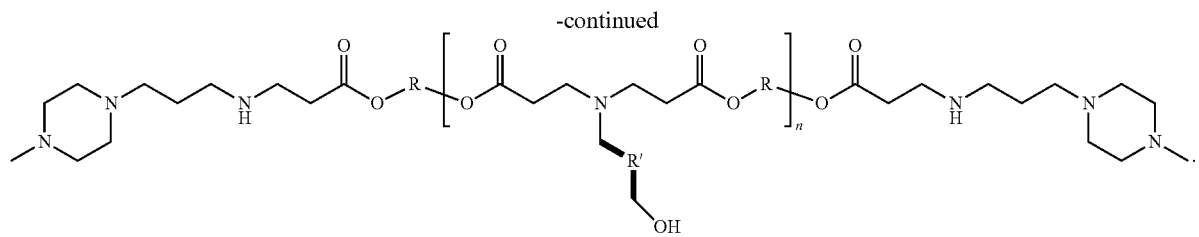

In other embodiments, the presently disclosed subject matter provides a method for forming a polyplex comprising DNA or siRNA, the method comprising diluting a blend of a polyethylene glycol (PEG)-b-poly(β-amino ester) (PBAE) co-polymer and a poly(β-amino ester) (PBAE) in a solvent at a concentration at a weight-to-weight ratio with DNA or siRNA to form a polyplex comprising DNA or siRNA. In particular embodiments, the weight-to-weight ratio of PEG-PBAE-PEG and PBAE is selected from the group consisting of 1:2, 1:1, and 2:1.

III. Poly(β-Amino Ester)-Co-Polyethylene Glycol (PEG-PBAE-PEG) Polymers for Gene and Drug Delivery In other embodiments, the presently disclosed compositions, in some embodiments, can be used to deliver drugs, genes, and other pharmaceutical or therapeutic agents safely and effectively to different sites in the body and to different cells, such as cancer cells. In further embodiments, a blend of PEG-PBAE-PEG and PBAE can be used at various mass ratios to form polyplexes for gene delivery applications. Unique PBAE structures also are utilized to form the copolymers.

Accordingly, in some embodiments, the presently disclosed subject matter provides a method for treating a disease or condition, the method comprising administering to a subject in need of treatment thereof, a compound of Formula (I) or a pharmaceutical composition thereof, comprising a pharmaceutical or therapeutic agent effective for treating the disease or condition. In some embodiments, the disease or condition is selected from the group consisting of cancer, including brain cancer (including Glioblastoma Multiforme), lung cancer, breast cancer, prostate cancer, colorectal cancer, and other cancers; cardiovascular diseases; infectious diseases; and ophthalmic diseases, including age-related macular degeneration.

In other embodiments, the presently disclosed subject matter provides a method for delivering a therapeutic agent to a cell, a specific cell line, a tissue, or an organism, the method comprising associating a pharmaceutical or therapeutic agent with a compound of Formula (I), or a pharmaceutical composition thereof, to form one or more particles, micelles, or polyplexes comprising the agent and compound of Formula (I), and administering the one or more particles or contacting the one or more particles with the cell, specific cell line, tissue or organism. In particular embodiments, the therapeutic agent is selected from the group consisting of a gene, DNA, RNA, siRNA, miRNA, isRNA, agRNA, smRNA, a nucleic acid, a peptide, a protein, a chemotherapeutic agent, a hydrophobic drug, and a small molecule drug. In some embodiments, the cell comprises a cancer cell. In particular embodiments, the cancer cell comprises a breast cancer cell.

The presently disclosed polymers can be applied in any field where polymers have been found useful including, but not limited to, drug delivery and nucleic acid delivery. Accordingly, in some embodiments, the presently disclosed polymers provide for efficient intracellular delivery of therapeutic agents, such as nucleic acids, proteins, and the like, into cells. Thus, the presently disclosed polymers are well suited for the efficient delivery of DNA for non-viral gene delivery applications.

More particularly, the presently disclosed materials are useful for drug and gene delivery due, in part, to one or more of the following aspects: (a) an ability to bind and encapsulate cargos including, but not limited to, DNA, siRNA, peptides, and proteins; (b) an ability to facilitate uptake of the cargos into a range of cell types, with differential cell-type specificity. Being able to tune delivery to certain cell types based on small molecule changes to the ends of the polymers are one aspect of the presently disclosed subject matter; (c) an ability to promote endosomal escape to protect the cargos from degradation and enhance delivery to the cytoplasm or alternatively, an ability to direct delivery to the endosome or other compartments; (d) the materials are degradable, which enables triggered intracellular drug release of a given cargo to be tuned to promote optimal delivery to the target cell type of interest. In some embodiments, the presently disclosed compounds comprise linkages that are broken due to the presence of water and the rates of degradation can be further tuned by other molecules that act as catalysts; (e) the materials are not cytotoxic; and (f) the materials have a large potential for structural diversity.

Accordingly, in some embodiments, the presently disclosed degradable, cationic polymers can be used to deliver one or more therapeutic agents, biomolecules or small molecules to a cell, tissue, and/or organism either in vitro or in vivo. Representative therapeutic agents, biomolecules or small molecules include, but are not limited to, DNA, RNA (siRNA, miRNA, isRNA, agRNA, smRNA, and the like), nucleic acids, peptides, proteins, hydrophobic drugs, and small molecules.

Such embodiments can be used to treat various conditions or diseases including, but not limited to, cancer, including brain cancer (including Glioblastoma Multiforme), lung cancer, and other cancers; cardiovascular diseases; infectious diseases; ophthalmic diseases, including age-related macular degeneration. The presently disclosed polymers also can be used as a genetic vaccine or as artificial antigen presenting cells; as an adjuvant; as an immunosuppressant; as an immune system modulator; as agents for cell targeting; for enhancement of crops; enhancement of animals; and other therapeutic use in humans.

In some embodiments, the presently disclosed polymers are put together as a kit for the delivery of an agent, a nucleic acid, DNA, or RNA to a specific cell line or to any non-specified type of cell. In further embodiments, the presently disclosed polymers can be put together as a kit for the delivery of agents to specific cells to generate induced pluripotent stem cells. In some embodiments, the presently disclosed polymers can be put together as a kit for the delivery of agents to stem cells to control their growth, differentiation, and/or development.

The presently disclosed biomaterials (linear or branched oligomers, polymers, or cross-linked polymers) also can be useful for other applications, including, but not limited to, coatings for particles or devices via electrostatic or covalent interactions with the particles or surfaces. Such devices include, but are not limited to, nanoparticles, microparticles, stents, stent-like devices, and the like. Such coated devices also could be included in kits for screening or assay development.

Accordingly, in some embodiments, the presently disclosed polymers can be used to coat surfaces for biomedical applications or environmental applications, including, but not limited to, coating devices such as stents, stent-like devices, implants, or other biomedical or drug delivery devices. In some embodiments, multilayered coatings comprising 1-10 polymer layers; in some embodiments, 11-20 polymer layers; in some embodiments, 21-30 polymer layers; in some embodiments, 31-50 polymer layers; in some embodiments, 51-100 polymer layers; and in some embodiments, greater than 100 polymer layers.

In some embodiments, the presently disclosed polymers can be used as cosmetic products. In other embodiments, the presently disclosed polymers can be used as dental products In certain embodiments, the degradation products or the presently disclosed polymers are bioactive. In some embodiments, the degradation products are drugs and/or pro-drugs. In other embodiments, the degradation products facilitate organelle targeting. In yet other embodiments, the degradation products facilitate nuclear targeting.

In certain embodiments, nanoparticles formed through the presently disclosed procedures that encapsulate active agents (such as DNA, siRNA, peptide, and proteins) are themselves encapsulated into a larger microparticle or device. In some embodiments, this larger structure is degradable and in other embodiments it is not degradable and instead serves as a reservoir that can be refilled with the nanoparticles. These microparticles and/or devices can be constructed with any biomaterials and methods that one skilled in the art would be aware. In some embodiments they can be constructed with multi-component degradable cationic polymers as described herein. In other embodiments, they can be constructed by FDA approved biomaterials, including, but not limited to, poly(lactic-co-glycolic acid) (PLGA). In the case of PLGA and the double emulsion fabrication process as an example, the nanoparticles are part of the aqueous phase in the primary emulsion. In the final PLGA microparticles, the nanoparticles will remain in the aqueous phase and in the pores/pockets of the PLGA microparticles. As the microparticles degrade, the nanoparticles will be released, thereby allowing sustained release of the nanoparticles.

In certain embodiments, the nanoparticle targeting (through biomaterial selection, nanoparticle biophysical properties, and/or a targeting ligand) will be combined with transcriptional targeting. Transcriptional targeting includes designing a promoter so that the delivered nanoparticles carrying a nucleic acid cargo are only active in the cells or tissue types of interest. In one particular example applied to treating brain cancer, combinations of different genetic cargos and/or particles are co-delivered simultaneously to deliver nucleic acids that both: (1) induce apoptosis (genes for tumor necrosis factor-related apoptosis-inducing ligand (TRAIL), p53, and the like) and (2) cause differentiation of cancer stem cells (Bone morphogenetic protein 4 (BMP-4) DNA, Glycogen synthase kinase 3beta shRNA/siRNA, and the like). These nucleic acids are driven by brain cancer specific promoters, such as Nestin and Sox-2 for brain cancer stem cells and Glial fibrillary acid protein (GFAP) for glia.

In some embodiments, the presently disclosed subject matter also includes a method of using and storing the polymers and particles described herein whereby a cryoprotectant (including, but not limited to, a sugar) is added to the polymer and/or particle solution and it is lyophilized and stored as a powder. Such a powder is designed to remain stable and be reconstituted easily with aqueous buffer as one skilled in the art could utilize.

IV. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

A named "R" or group will generally have the structure that is recognized in the art as corresponding to a group having that name, unless specified otherwise herein. For the purposes of illustration, certain representative "R" groups as set forth above are defined below.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom. Representative alkyl groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, and the like, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls. Alkyl groups can optionally be substituted (a "substituted alkyl") with one or more alkyl group substituents, which can be the same or different. The term "alkyl group substituent" includes but is not limited to alkyl, substituted alkyl, halo, acylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propyne, 3-hexyne, and the like.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, alkenyl, alkynyl, aryl, substituted aryl, aralkyl, hydroxyl, alkoxyl, aryloxyl, aralkyloxyl, carboxyl, acyl, halo, haloalkyl, nitro, alkoxycarbonyl, aryloxycarbonyl, aralkoxycarbonyl, acyloxyl, amino, alkylamino, dialkylamino, trialkylamino, acylamino, aroylamino, carbamoyl, cyano, alkylcarbamoyl, dialkylcarbamoyl, carboxyaldehyde, carboxyl, alkoxycarbonyl, carboxamide, arylthio, alkylthio, alkylene, thioalkoxyl, and mercapto.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The terms "heteroaryl" and "aromatic heterocycle" and "aromatic heterocyclic" are used interchangeably herein and refer to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl) amino)ethyl)piperazine, 4-(2-(diethylamino)ethyl)piperazine, 4-(2-chlorophenyl)piperazine, 4(2-cyanophenyl)piperazine, 4-(2-ethoxyphenyl)piperazine, 4-(2-ethylphenyl) piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4(2-nitrophenyl) piperazine, 4-(2-nitrophenyl)piperazine, 4-(2-phenylethyl) piperazine, 4-(2-pyridyl)piperazine, 4-(2-pyrimidinyl) piperazine, 4-(2,3-dimethylphenyl)piperazine, 4-(2,4-difluorophenyl) piperazine, 4-(2,4-dimethoxyphenyl) piperazine, 4-(2,4-dimethylphenyl)piperazine, 4-(2,5-dimethylphenyl)piperazine, 4-(2,6-dimethylphenyl) piperazine, 4-(3-chlorophenyl)piperazine, 4-(3-methylphenyl)piperazine, 4-(3-trifluoromethylphenyl) piperazine, 4-(3,4-dichlorophenyl)piperazine, 4-3,4-dimethoxyphenyl)piperazine, 4-(3,4-dimethylphenyl) piperazine, 4-(3,4-methylenedioxyphenyl)piperazine, 4-(3, 4,5-trimethoxyphenyl)piperazine, 4-(3,5-dichlorophenyl) piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl) piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl) piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl) piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole. The heteroaryl ring can be fused or otherwise attached to one or more heteroaryl rings, aromatic or non-aromatic hydrocarbon rings, or heterocycloalkyl rings. A structure represented generally by the formula:

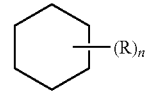

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

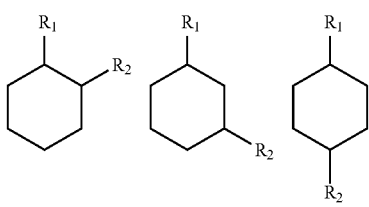

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxy, n-hexoxy, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$.

"Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R" ', wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

Further, as used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 μm). In such embodiments, the particle also can be referred to as a "microparticle. Thus, the term "microparticle" includes particles having at least one dimension in the range of about one micrometer (μm), i.e., $1 \times 10^{-6}$ meters, to about 1000 μm. The term "particle" as used herein is meant to include nanoparticles and microparticles.

It will be appreciated by one of ordinary skill in the art that nanoparticles suitable for use with the presently disclosed methods can exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. In particular embodiments, the presently disclosed nanoparticles have a spherical shape.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

"PBAE": As used herein, the abbreviation "PBAE" refers to a poly(β-amino ester) (PEG-PBAE). The PBAE may be further referred to by using nomenclature indicating the monomers used to prepare the PBAE, with "B" designating the monomer comprising the "backbone" of the polymer; "S" designating the side chain; and "E" designating the end group. For example, the abbreviation "B4S4E7" would indicate a PBAE having a "B4" monomer backbone, an "S4" monomer side chain, and an "E7" monomer end group. The PBAE "B4S4E7" also can be referred to herein as "447." The same nomenclature conventions are used throughout for other PBAEs, as well.

The PBAE subunit of the presently disclosed PEG-PBAE-PEG block copolymers also can have associated with it a particular molecular weight in Daltons. For example, in the $PEG_{0.8k}$-$B4S4_{4k}$-$PEG_{0.8k}$ copolymer, the B4S4 PBAE subunit has a molecular weight of 4 kDa.

"PEG": As used herein, the abbreviation "PEG" refers to polyethylene glycol. The polyethylene may be further modified as disclosed herein, for example, with a thiol (—SH) containing moiety. Further, the PEG subunit of the presently disclosed PEG-PBAE-PEG block copolymers also can have associated with it a particular molecular weight in Daltons. For example, in the $PEG_{0.8k}$-$B4S4_{4k}$-$PEG_{0.8k}$ copolymer, the PEG subunits have a molecular weight of 0.8 kDa. This copolymer also can be referred to herein as "0.8k-4k." See Table 1.

Representative monomers for use with the presently disclosed PEG-PBAE-PEG block copolymers in addition to the monomers disclosed herein include, but are not limited to the following:

B3 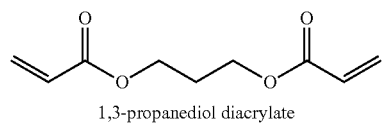
1,3-propanediol diacrylate

B3b 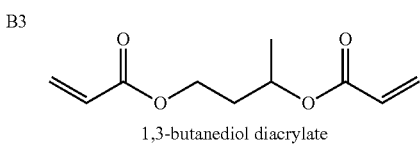
1,3-butanediol diacrylate

B4 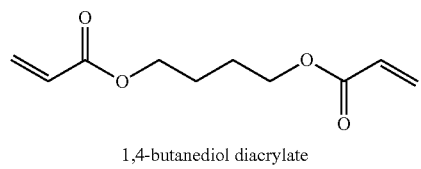
1,4-butanediol diacrylate

B5 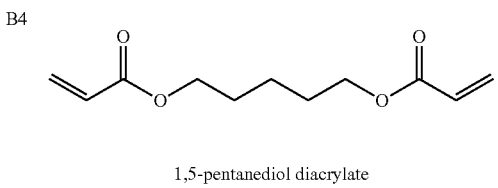
1,5-pentanediol diacrylate

B6 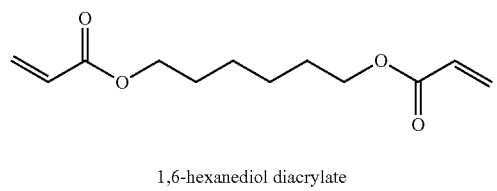
1,6-hexanediol diacrylate

B8 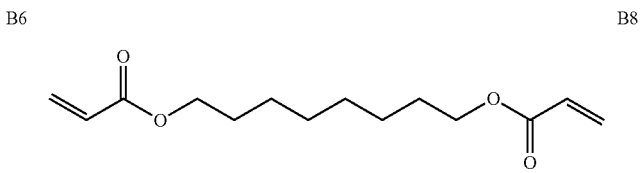
1,8-octanediol diacrylate

BSS 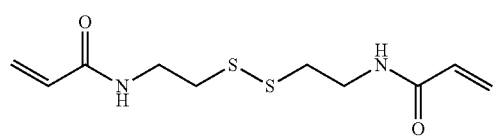
N,N′-bis(acrylyl)cystamine

BL1 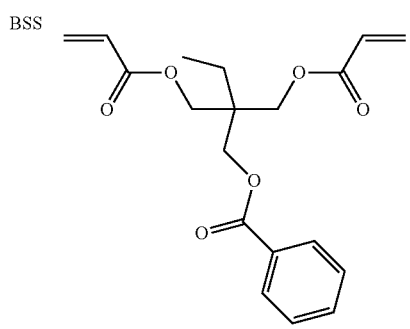
trimethylolpropane benzoate diacrylate

BL2 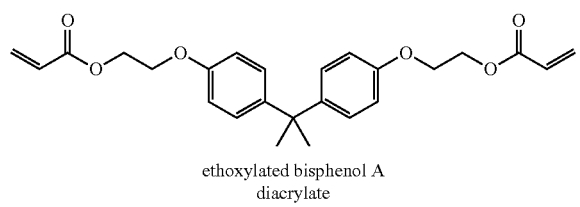
ethoxylated bisphenol A diacrylate

BH1 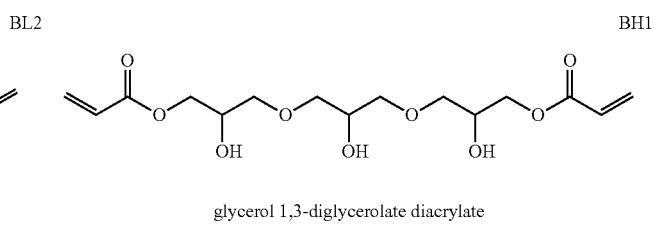
glycerol 1,3-diglycerolate diacrylate

BP1 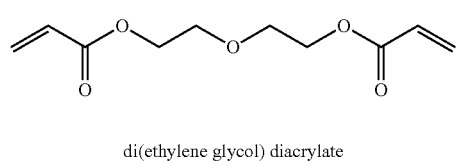
di(ethylene glycol) diacrylate

BP2 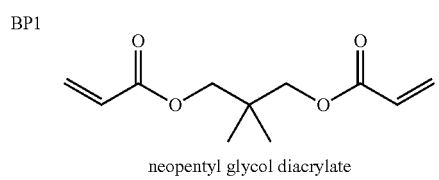
neopentyl glycol diacrylate

BP3 

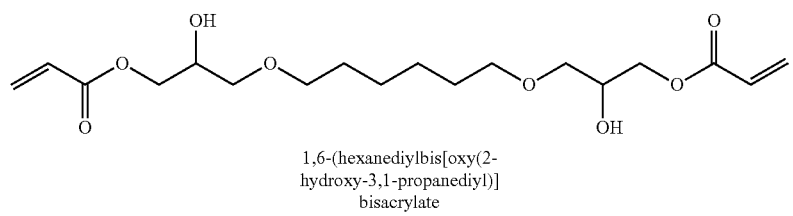
1,6-(hexanediylbis[oxy(2-hydroxy-3,1-propanediyl)] bisacrylate

-continued

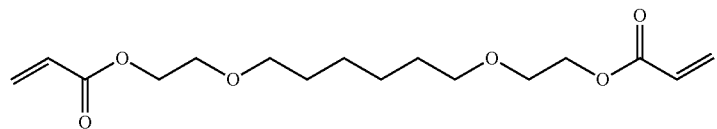
2,2′-(hexane-1,6-diylbis(oxy))bis(ethane-2,1-diyl) diacrylate
BP4

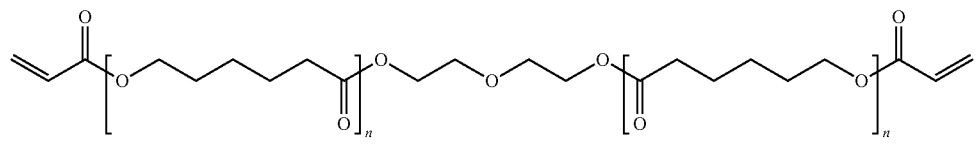
polycaprolactone diacrylate
BP6

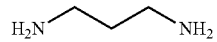
propane-1,3-diamine
E1

2,2-dimethylpropane-1,3-diamine
E2

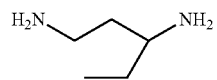
pentane-1,3-diamine
E3

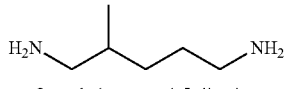
2-methylpentane-1,5-diamine
E4

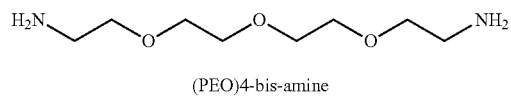
(PEO)4-bis-amine
E5

2-(3-aminopropylamino)ethanol
E6

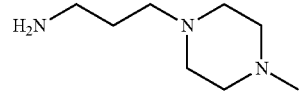
1-(3-aminopropyl)-4-methylpiperazine
E7

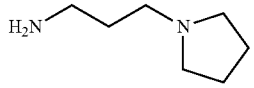
1-(3-aminopropyl)pyrrolidine
E8

3-amino-1-propanol
S3

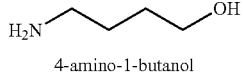
4-amino-1-butanol
S4

5-amino-1-pentanol
S5

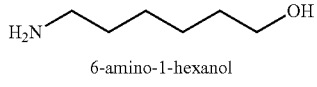
6-amino-1-hexanol
S6

3-aminopropane-1,2-diol
S7

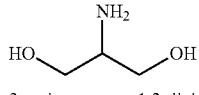
2-aminopropane-1,3-diol
S8

4-aminophenyl disulfide
E9

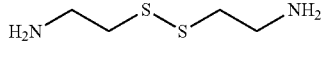
cystamine
E10

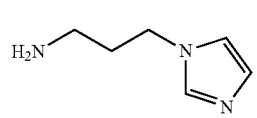
N-(3-aminopropyl)-imidazole
E11

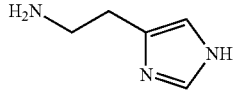
histamine
E12

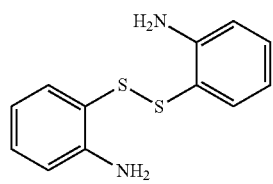
2,2'-dithiobis-benzenamine
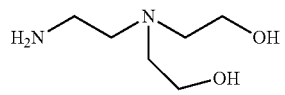
2,2'-(2-aminoethylazanediyl)diethanol
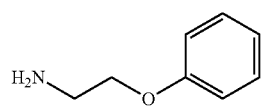
2-phenoxyethanamine
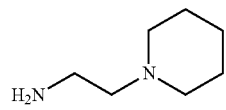
1-(2-aminoethyl)piperidine
-continued
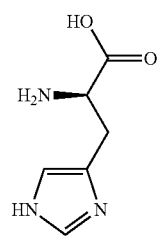
D-histidine
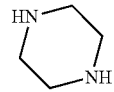
piperazine
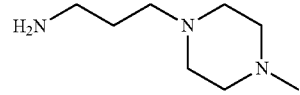
1-(3-aminopropyl)-4-methylpiperazine
In some embodiments, the end group "E" is selected from the group consisting of:
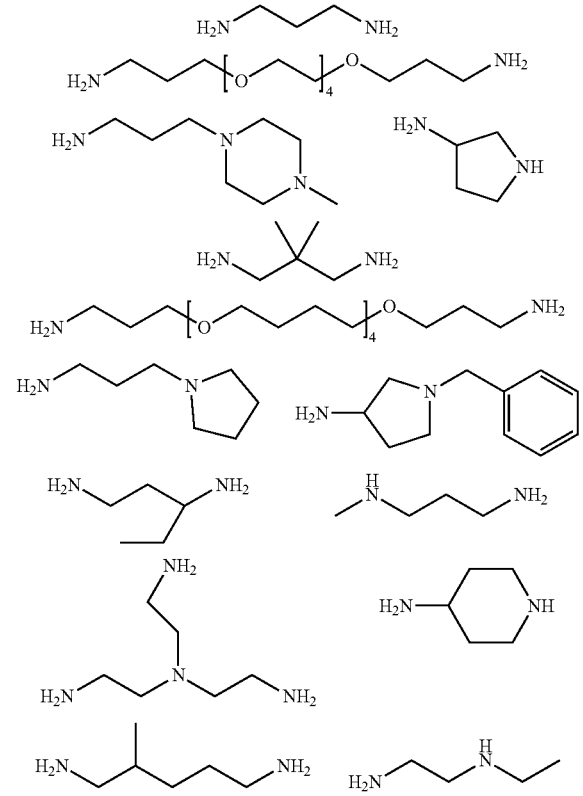
-continued
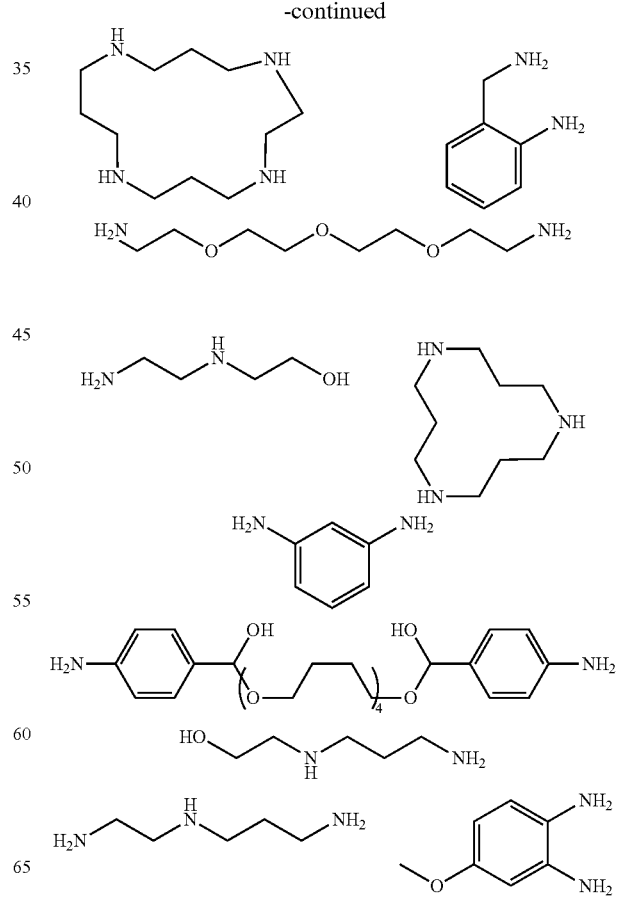

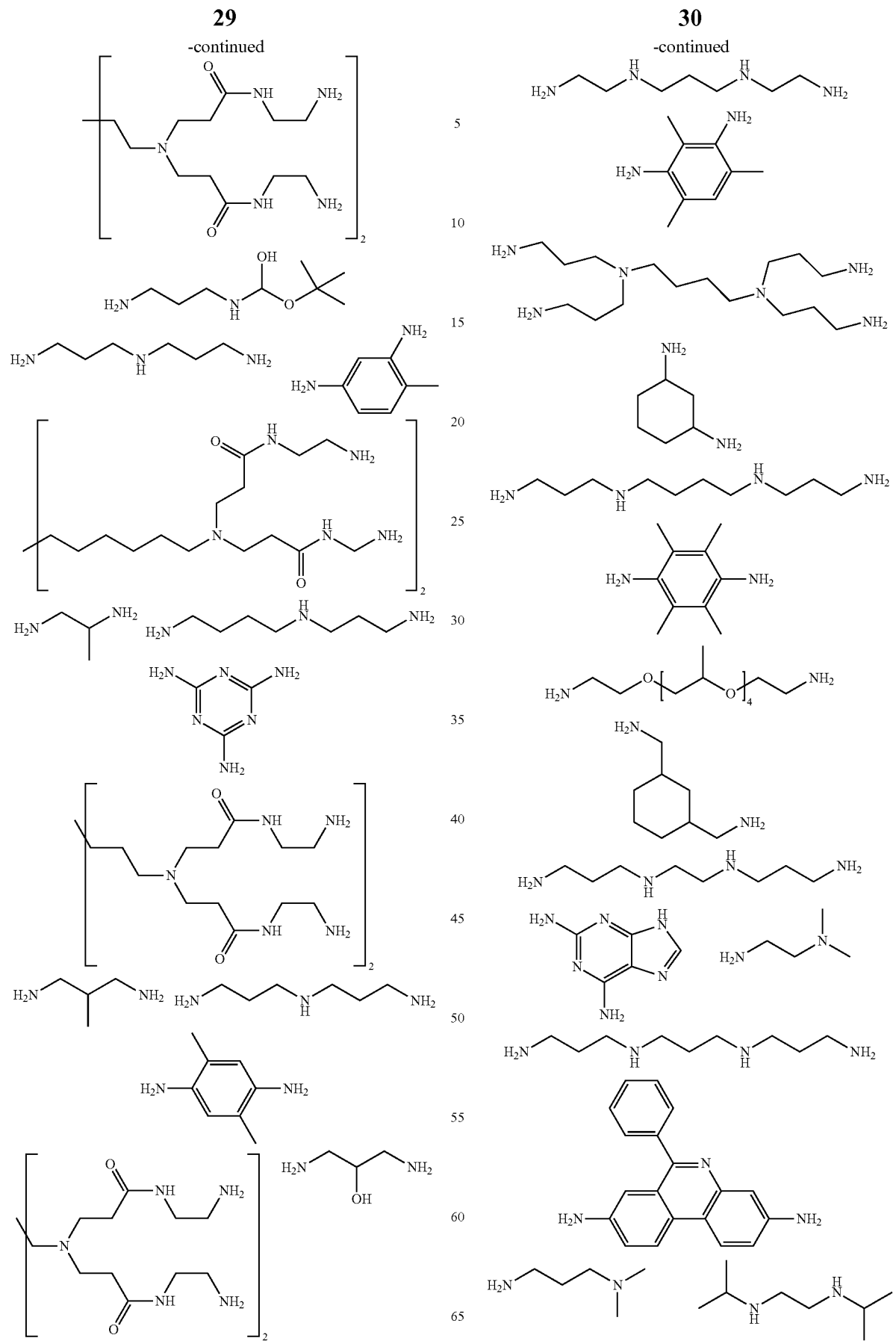

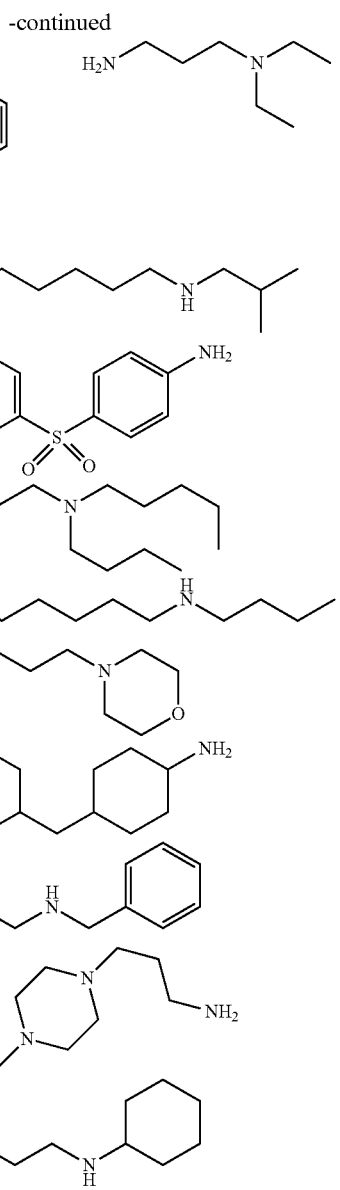

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

"Peptide" or "protein": A "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, and the like. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis and Application of Poly(Ethylene Glycol)-Co-Poly(β-Amino Ester) Copolymers for Small Cell Lung Cancer Gene Therapy The design of non-viral polymeric nanoparticles for successful gene therapy requires engineering of the polymer structure to overcome barriers at multiple levels, including prolonged colloidal stability during formulation and therapeutic use. Poly(β-amino ester)s (PBAEs) have been shown to be effective as polymeric vectors for intracellular delivery of DNA, but limited studies have focused on polymer modifications to enhance the stability of PBAE/DNA polyplexes. The presently disclosed subject matter, in some embodiments, provides block copolymers comprising PBAE oligomer center units and poly(ethylene glycol) (PEG) end units, synthesized via thiolene Michael addition. A library of PEG-PBAE polyplexes were prepared by blending PEGylated PBAEs and non-PEGylated PBAEs of different polymer structures, different molecular weights of PEG, and at different mass ratios of cationic polymer to anionic DNA.

Non-PEGylated PBAE polyplexes were found to aggregate following a 24-h incubation in both acidic buffer and in physiological buffer, presenting a challenge for therapeutic use.

In contrast, among 36 PEG-PBAE polyplex formulations evaluated, certain PEG-PBAE polyplexes maintained a small size through 24-h incubations under these conditions. These selected polyplexes were further evaluated for transfection in human small cell lung cancer cells (H446) in the presence of serum, and the best polyplex formulation transfected approximately 40% of these hard-to-transfect cells while also preventing polymer-mediated cytotoxicity.

When this PEG-PBAE polyplex delivered Herpes simplex virus thymidine kinase plasmid in combination with the prodrug ganciclovir, 35% of H446 human small cell lung cancer cells were killed in comparison to just 15% of healthy human lung fibroblasts (IMR-90) as control cells.

The presently disclosed subject matter indicates that PEG-PBAE polyplexes can maintain particle stability without compromising their therapeutic function for intracellular delivery to human small cell lung cancer cells, demonstrate potential cancer specificity, and have potential as safe and biodegradable materials for use in small cell lung cancer gene therapy.

Example 2

Overview

Small cell lung cancer (SCLC) is a neuroendocrine subtype of lung cancer that accounts for 15% of all lung cancer cases. E. Rodriguez, R. C. Lilenbaum. Small cell lung cancer: past, present, and future Curr Oncol Rep, 12 (2010): 327-34. SCLC is initially sensitive to chemotherapy and radiation, most often involving a combination of cisplatin-etoposide chemotherapy with chest radiation, prophylactic cranial irradiation, or hyperfractionated thoracic radiation. A. Paumier, C. Le Pechoux. Radiotherapy in small-cell lung cancer: where should it go? Lung Cancer, 69 (2010):133-40. However, SCLC still has one of the highest fatality rates among cancers due to its high recurrence and metastasis. R. Siegel, D. Naishadham, A. Jemal. Cancer statistics, 2012 C A Cancer J Clin, 62 (2012):10-29; A. M. Brade, I. F. Tannock. Scheduling of radiation and chemotherapy for limited-stage small-cell lung cancer: repopulation as a cause of treatment failure? J Clin Oncol, 24 (2006):1020-2. Accordingly, new therapies are needed to improve the survival of patients with SCLC.

Gene therapy is a promising technology due to its tremendous potential as a selective and potent therapeutic for genetic diseases including cancer. Although viral vectors have the advantage of high transduction efficacy, limitations in cargo capacity, difficulty of production, and safety concerns due to immunogenic and mutagenic factors have led to the emergence of non-viral approaches as alternatives. T. Hollon. Researchers and regulators reflect on first gene therapy death Nat Med, 6 (2000):6; D. W. Pack, A. S. Hoffman, S. Pun, P. S. Stayton. Design and development of polymers for gene delivery Nat Rev Drug Discov, 4 (2005): 581-93.

Poly(β-amino ester)s (PBAEs), a class of biodegradable cationic polymers, have been shown to exhibit low levels of toxicity and high rates of both DNA and siRNA transfection in various types of cells. D. G. Anderson, A. Akinc, N. Hossain, R. Langer. Structure/property studies of polymeric gene delivery using a library of poly(beta-amino esters) Mol Ther, 11(2005):426-34; N. S. Bhise, K. J. Wahlin, D. J. Zack, J. J. Green. Evaluating the potential of poly(beta-amino ester) nanoparticles for reprogramming human fibroblasts to become induced pluripotent stem cells Int J Nanomedicine, 8 (2013):4641-58; S. W. Cho, F. Yang, S. M. Son, H. J. Park, J. J. Green, S. Bogatyrev, et al. Therapeutic angiogenesis using genetically engineered human endothelial cells J Control Release, 160 (2012):515-24; S. Y. Tzeng, J. J. Green. Subtle changes to polymer structure and degradation mechanism enable highly effective nanoparticles for siRNA and DNA delivery to human brain cancer Adv Healthc Mater, 2 (2013):468-80; R. E. Vandenbroucke, B. G. DeGeest, S. Bonne, M. Vinken, T. Van Haecke, H. Heimberg, et al. Prolonged gene silencing in hepatoma cells and primary hepatocytes after small interfering RNA delivery with biodegradable poly(beta-amino esters) J Gene Med, 10 (2008): 783-94. These cationic polymers are able to bind with negatively charged nucleotides and form polyplexes by electrostatic interactions.

Previous studies have shown that the biophysical properties of these PBAE polyplexes allow them to overcome critical barriers to gene delivery at the cellular level, including cellular uptake and endosomal escape via pH buffering. C. J. Bishop, T. M. Ketola, S. Y. Tzeng, J. C. Sunshine, A. Urtti, H. Lemmetyinen, et al. The effect and role of carbon atoms in poly(beta-amino ester)s for DNA binding and gene delivery J Am Chem Soc, 135(2013):6951-7; J. C. Sunshine, D. Y. Peng, J. J. Green. Uptake and transfection with polymeric nanoparticles are dependent on polymer end-group structure, but largely independent of nanoparticle physical and chemical properties Mol Pharm, 9 (2012): 3375-83. However, there has been limited effort to modify PBAE polyplexes to promote biological stability in vitro and in vivo. T. J. Harris, J. J. Green, P. W. Fung, R. Langer, D. G. Anderson, S. N. Bhatia. Tissue-specific gene delivery via nanoparticle coating Biomaterials, 31 (2010):998-1006.

Poly(ethylene glycol) (PEG), a water-soluble molecule with low toxicity, is widely used with a variety of biomaterials to minimize unwanted interactions with biomolecules. Its neutral and hydrophilic structure not only reduces surface charge of particles but also provides steric hindrance to reduce non-specific adsorption and aggregation. These properties have been shown to significantly enhance stability and increase half-life of biologics and particles in systemic circulation. J. M. Harris, R. B. Chess. Effect of pegylation on pharmaceuticals Nat Rev Drug Discov, 2 (2003):214-21; D. E. Owens, 3rd, N. A. Peppas. Opsonization, biodistribution, and pharmacokinetics of polymeric nanoparticles Int J Pharm, 307 (2006):93-102.

The presently disclosed subject matter provides a novel synthesis method to conjugate PEG to PBAE polymers and shows that polyplexes can be prepared with a blend of PEGylated PBAEs (PEG-PBAEs) and end-capped PBAEs (ePBAEs), S. Y. Tzeng, J. J. Green. Subtle changes to polymer structure and degradation mechanism enable highly effective nanoparticles for siRNA and DNA delivery to human brain cancer Adv Healthc Mater, 2 (2013):468-80; J. C. Sunshine, M. I. Akanda, D. Li, K. L. Kozielski, J. J. Green. Effects of base polymer hydrophobicity and end-group modification on polymeric gene delivery Biomacromolecules, 12 (2011):3592-600, to maintain particle stability and efficacy over time. We also demonstrate that these polyplexes can deliver Herpes simplex virus thymidine kinase (HSV-tk) gene in vitro and activate ganciclovir to kill SCLC cells.

Example 3

Materials and Methods

Materials 1,4-butanediol diacrylate (B4), 4-amino-1-pentanol (S4), 5-amino-1-pentanol (S5), 1-(3-aminopropyl)-4-methylpiperazine (E7) (Alfa Aesar), 1,5-pentanediol diacrylate (B5) (Monomer Polymer & Dajac Labs), 2-methylpentane-1,5-diamine (E4) (TCI America), 2-(3-aminopropylamino)ethanol (E6) (Fluka), poly(ethylene glycol) methyl ether thiol (800 Da), branched 25 kDa poly(ethylenimine) (PEI) (Sigma-Aldrich), α-Mercaptoethyl-ω-methoxy polyoxyethylene (5000 Da) (NOF America Corporation), and cell culture media components were purchased and used as received. pEGFP-N1 (EGFP) DNA (purchased from Elim Biopharmaceuticals and amplified by Aldevron, Fargo, N. Dak.), ganciclovir (Invivogen, San Diego, Calif.), Label IT-Tracker Cy3 kit (Minis Bio LLC), and CellTiter 96 AQueous One MTS assay (Promega, Fitchburg, Wis.) were obtained from commercial vendors and used per manufacturer's instructions. HSV-tk gene was cloned into the pcDNA3.1 vector (Life Technologies) and amplified (Aldevron, Fargo, N. Dak.).

Example 4

Polymer Synthesis and Characterization

The presently disclosed ePBAEs and PEG-PBAEs were synthesized in a two-step reaction using small commercially-available molecules as described in FIG. 2A. As an example, acrylate terminated base polymer poly(1,4-butanediol diacrylate-co-4-amino-1-butanol) (B4S4) was first synthesized by mixing a backbone monomer (B4) and a side-chain monomer (S4) at 1.2:1 or 1.05:1 B4:S4 monomer molar ratios in DMSO as a 500 mg/mL solution and stirring at 90° C. for 24 h. The base polymer was purified in cold diethyl ether, dried under vacuum with desiccant for 24 h, and the molecular weight and chemical structure of the base polymer were confirmed by Bruker Avance III 500 MHz NMR spectrometer in $CDCl_3$. Base polymers were end-capped with a small molecule (E4, E6, or E7) by dissolving base polymer and end-capping molecule at 1:30 molar ratio in THF as a 100 mg/mL solution and shaking the mixture at room temperature for 3 h. Final ePBAE polymers were purified in cold diethyl ether, dried under vacuum with desiccant for 24 h, confirmed with 1H NMR for complete conjugation, and then stored with desiccant at −20° C. as 100 mg/mL solutions in DMSO.

Amine-catalyzed, thiolene Michael addition reaction was used to conjugate PEG to the base polymer B4S4. J. Vandenbergh, K. Ranieri, T. Junkers. Synthesis of (Bio)-Degradable Poly(β-thioester)s via Amine Catalyzed Thiolene Click Polymerization Macromolecular Chemistry and Physics, 213 (2012):2611-7. Briefly, B4S4, methoxy PEG-thiol, and E7 molecules were mixed at 1:2.5:0.2 molar ratios as a 100 mg/mL solution in DMSO and stirred at room temperature for 24 h at 1000 rpm. Final block copolymers were precipitated in diethyl ether at room temperature without centrifugation, confirmed with 1H NMR for complete conjugation, and stored with desiccant at −20° C. as 100 mg/mL solutions in DMSO.

Gel permeation chromatography and 1H NMR analysis confirmed structure and PEGylation from the absence of acrylate peaks (FIG. 1A). The micelles formed were 110 nm as determined using Nanosight Nanoparticle Tracking Analysis (NTA) to confirm particle formation (FIG. 1B). The micelles maintained their size and avoided significant aggregation even after 24 hours, suggesting that the particles are highly stable.

The nomenclature of PEG-PBAEs disclosed herein is listed in Table 1.

TABLE 1

Nomenclature of representative PEG-PBAE polymers. The PBAE used was 1-4-butanediol diacrylate-co-1,4-aminobutanol (B4S4).

| PEG-PBAE | Name |
|---|---|
| $PEG_{0.8k}$-$B4S4_{4k}$-$PEG_{0.8k}$ | 0.8k-4k |
| $PEG_{0.8k}$-$B4S4_{13k}$-$PEG_{0.8k}$ | 0.8k-13k |
| $PEG_{5k}$-$B4S4_{4k}$-$PEG_{5k}$ | 5k-4k |
| $PEG_{5k}$-$B4S4_{13k}$-$PEG_{5k}$ | 5k-13k |

Example 5

Particle Formulation and Characterization

PBAE polyplexes were made at 60 and 75 w/w mass ratios of ePBAE to DNA in 25 mM sodium acetate buffer (pH=5). For example, diluted polymer solution at 3.6 mg/mL was mixed into diluted DNA solution at 0.06 mg/mL at equal volume to form 60 w/w polyplexes, and the mixture was incubated for 10 minutes to allow complexation. 75 w/w was tested to check for cytotoxicity of ePBAE at higher polymer concentration. PEG-PBAE polyplexes were made at 30, 60, 90 w/w ratios of total polymer to DNA in 25 mM sodium acetate buffer (pH=5). Polymer used to condense DNA was a mixture of ePBAE and PEG-PBAE at three different mass ratios of 1:2, 1:1, and 2:1. For example, 50 μg of ePBAE 447 and 100 μg of PEG-PBAE 5k-4k were diluted to 3.6 mg/mL total polymer concentration with 25 mM sodium acetate buffer (pH=5), and the polymer solution was mixed with diluted DNA solution at 0.06 mg/mL at equal volume to form polyplexes with 447:5k-4k 1:2 w/w and polymer:DNA 60 w/w ratios. These polyplexes were incubated for 10 minutes to allow complexation.

The polyplex size was determined by nanoparticle tracking analysis (NTA) using Nanosight NS500 (Malvern Instruments, 532 nm laser) and dynamic light scattering (DLS) using Malvern Zetasizer Nano ZS (Malvern Instruments, detection angle 173°, 633 nm laser). The polyplexes prepared at DNA concentration of 0.1 mg/mL were diluted 1000-fold and 2-fold into 25 mM sodium acetate buffer or 2×PBS to a total volume of 400 μL for Nanosight and Zetasizer, respectively. To determine 24 h stability of the polyplexes, cuvettes with the polyplex solution were stored in dark at room temperature for 24 h, then the polyplex size was re-measured following a brief resuspension. Only number-weighted measurements with particle concentrations above 15 particles/frame by NTA and intensity-weighted Z-average measurements passing the quality control expert advice criteria by DLS are reported. Zeta potential was determined using Malvern a Zetasizer Nano ZS (Malvern Instruments) with samples prepared at DNA concentration of 0.03 mg/mL diluted 2-fold into 25 mM sodium acetate buffer (pH=5.0) for a total volume of 800 The mean and standard deviation were calculated.

Example 6

Cell Culture

H446 small cell lung cancer cells (ATCC) were cultured at 37° C. and 5% $CO_2$ in ATCC-modified RPMI 1640 media (Life Technologies A10491-01), supplemented with 10% FBS and 1% penicillin/streptomycin. IMR-90 human lung fibroblast cells (ATCC) were cultured at 370 C and 5% $CO_2$ in Eagle's minimum essential media (Cellgro 10-009-CV), supplemented with 10% FBS.

Example 7

DNA Delivery Assays 2.5.1. Polyplex Delivery

Cells were plated at a density of 15,000 cells/well (100 μL/well) in 96-well tissue culture plates and were incubated for 24 h. pEGFP labeled with Cy3 per manufacturer's instructions (Label IT Tracker kit) and unlabeled pEGFP were used for uptake and transfection experiments, respectively. Polyplexes were prepared as described above to a final DNA concentration of 0.03 mg/mL. Then, 20 μL of polyplexes was added to 100 μL of serum-containing medium in each well. For PEI polyplexes, pEGFP-Cy3 diluted into 150 mM NaCl to 60 μg/mL was mixed with equal volume of PEI diluted into 150 mM NaCl to 120 μg/mL (2 w/w) from a stock solution of 1 mg/mL in dH2O. PEI polyplexes were also incubated for 10 min to complex, and 20 μL of polyplex solution was added to 100 μL of medium in each well. For uptake experiments, cells were incubated with polyplexes for 4 h, washed twice with heparin-containing PBS (50 μg/mL), and prepared for flow cytometry. For transfection experiments, cells were incubated with polyplexes for 4 h, washed twice with heparin-containing PBS, and incubated with 100 μL fresh media for an additional 48 h before analyzing with FACS analysis and taking fluorescent images.

2.5.2. Cell Viability

Cells were treated following the same protocol as transfection. Following 4 hours of incubation with polyplexes, cells were washed twice with heparin-containing PBS, added with 100 μL of fresh media, and incubated for an additional 24 h at 37° C. 20 μL of CellTiter 96 AqueousOne MTS reagent were added per well, cells were incubated with reagent at 370 C, and absorbance was measured at 490 nm using a Synergy 2 plate reader (Biotek) every 30 min until the highest absorbance signal reached 1.2. Absorbance signal was normalized to that of untreated cells after subtracting the background signal. All conditions were prepared in quadruplicates.

2.5.3. Flow Cytometry

To prepare for flow cytometry (Accuri C6 with HyperCyt high-throughput adaptor), cells were detached using 30 μL of 0.05% trypsin, resuspended with 170 μL of FACS buffer (PBS containing 2% v/v FBS), transferred to a round-bottom 96-well plate and centrifuged at 800 rpm at 40° C. for 5 min. 170 μL of supernatant was removed, and the remaining 30 μL was triturated to resuspend the cells. Propidium iodide (PI) (Invitrogen, Carlsbad, Calif.) was added to FACS buffer at 1:200 to detect cells in the process of apoptosis for transfection assay.

For uptake, % positive is the percentage of total cells that are Cy3+ as measured by two-dimensional gating of FL1 vs. FL2 using FlowJo 7.6.5 software. For transfection, % positive is the percentage of total cells that are EGFP+ as measured by sequential two dimensional gating of PI- by FSC-H vs. FL2 and EGFP+ by FL1 vs. FL2. At least 500 cell counts were analyzed for each measurement. All conditions were prepared in quadruplicates.

2.6 Delivery of pHSV-tk and Ganciclovir

Cells were treated following the same protocol as transfection using pHSV-tk DNA. Following 4 h of incubation with polyplexes, cells were washed twice with heparin-containing PBS and incubated with 100 μL of fresh media for 24 h at 370° C. The media was then replaced with fresh media containing 10 or 20 µg/mL of ganciclovir. Following additional 48 h incubation at 370° C., the media was replaced with fresh media containing 10 or 20 µg/mL of ganciclovir. Cell death was measured 24 h after the second ganciclovir treatment with CellTiter 96 AQueous CellTiter reagent as described above.

All conditions were prepared in quadruplicates. Stock ganciclovir solution at 5 mg/mL was prepared by dissolving it in 2% 1M NaOH, and then neutralizing the pH with 1% 1M HCl, 40% dH2O, and 57% 1×PBS by volume.

2.7. Statistics

All statistical analysis was performed with GraphPad Prism 5 software package. One-way ANOVA with post-hoc Dunnett test was used to test statistical significance of multiple conditions against the control group ($p<0.05$).

Example 8

Results

Synthesis and Characterization of PBAE and PEG-PBAE Polymer

An initial goal of the presently disclosed subject matter was to synthesize and confirm the molecular weight, as well as the complete the synthesis of ePBAEs and PEG-PBAEs. Both types of PBAEs share the same base polymer, with the molecular weight controlled by the molar ratio of backbone (B) to side-chain (S) monomers in the Step 1 reaction (FIG. 2A). Two molar ratios, 1.2:1 and 1.05:1, as well as two (B) and (S) monomer types each were used to synthesize four different acrylate-terminated base polymers with molecular weight distribution as shown in FIG. 3; the closer the monomer ratio is to unity, the greater the degree of polymerization.

A total of 9 ePBAEs were synthesized with three base polymers, B4S4, B4S5, and B5S5 of approximately 10 kDa, and three end-capping (E) molecules, E4, E6, and E7, by Step 2A end-capping reaction (FIG. 2A). Similar molecular weights were selected for each polymer structure. An example of an ePBAE nomenclature is 457, which is base polymer B4S5 end-capped with E7. A total of 4 PEG-PBAEs were synthesized with two base polymers (B4S4 at 4 and 13 kDa), and two methoxy PEG-thiol molecules (0.8 and 5 kDa). E7 was selected as the amine catalyst in this Step 2B PEGylation reaction because of its use for end-capping of PBAEs and its non-toxicity in previous studies. A. Mangraviti, S. Y. Tzeng, K. L. Kozielski, Y. Wang, Y. Jin, D. Gullotti, et al. Polymeric nanoparticles for nonviral gene therapy extend brain tumor survival in vivo ACS Nano, 9 (2015):1236-49. A trace amount of E7 (5% mol) was used to ensure PEGylation occurred and not E7-endcapping.

Because end-capping reactions involve a nucleophilic addition to acrylates, the completion of end-capping can be confirmed using 1H NMR. Once the diacrylates on the base polymer (FIGS. 4A and 4B) reacted with (E) molecules to yield ePBAE or with methoxy PEG-thiol molecules to yield PEG-PBAE (FIG. 4C), the signature peaks for protons on acrylates disappeared, verifying that every base polymer in the reaction was completely end-capped.

Preparation and Characterization of PEG-PBAE Polyplexes

Polyplexes are most often formulated via electrostatic interaction between cationic polymer and negatively charged DNA. Thus, N/P ratio, the ratio of amines in the polymer (N, positively charged) to phosphates in the DNA (P, negatively charged), is an important parameter for polyplex formulation. N/P ratio can also be converted to the total or the effective weight-to-weight ratio (w/w) between the polymer and the DNA, or vice versa, as long as the amine density and molecular weight are known. The total polymer: DNA w/w ratios that were used are converted to the effective PBAE:DNA w/w ratios and N/P ratios in Table 2. For PEG-PBAE polyplexes, ePBAE was also blended in with PEG-PBAE, and their weight to weight ratio was added as another parameter.

Polyplex stability over time was investigated with both nanoparticle tracking analysis (NTA) and dynamic light scattering (DLS) by measuring the increase in particle size over 24 h. While NTA directly measures the number-averaged hydrodynamic diameter, DLS reports an intensity-weighted average that is skewed towards larger or aggregated particles. Polyplex formulations that yielded significant aggregation or decomplexation as indicated by low particle concentration on NTA or large particle size over the detection limit on DLS were eliminated from further consideration as candidate gene delivery formulations (FIG. 5A). Four formulation conditions showed an initial particle size of 90-110 nm by NTA in both 25 mM sodium acetate buffer and PBS.

These small polyplex formulations were ePBAE blended with 5k-4k 1:2 30 w/w, 5k-4k 1:1 30 w/w, 5k-13k 1:2 30 w/w, and 5k-13k 1:1 30 w/w, and they were selected for subsequent transfection evaluation. While polyplexes with PEG-PBAE polymer synthesized from 4 kDa PBAE base polymer significantly aggregated over time in PBS, polyplexes with PEG-PBAE polymer synthesized from 13 kDa PBAE base polymer remained nanosized (approximately 300 nm) after 24 h incubation in PBS. All four formulations showed a slight decrease in surface charge to +7 mV in NaAc, although not statistically significant, in comparison to 447 60 w/w PBAE polyplexes (FIG. 5B).

TABLE 2

Chart for w/w to N/P conversion
($447_{13k}$ = 13 KDa MW ePBAE 447)

| Polymers | PBAE:PEG-PBAE w/w | Polymer:DNA w/w | Converted Polymer:DNA w/w | Converted N/P |
|---|---|---|---|---|
| $447_{13k}$ + $PEG_{0.8k}$-$44_{4k}$-$PEG_{0.8k}$ | 1:2 | 30 | 24.3 | 29.7 |
| | | 60 | 48.6 | 59.5 |
| | | 90 | 72.9 | 89.2 |
| $447_{13k}$ + $PEG_{0.8k}$-$44_{4k}$-$PEG_{0.8k}$ | 1:1 | 30 | 25.7 | 31.5 |
| | | 60 | 51.4 | 63.0 |
| | | 90 | 77.1 | 94.5 |
| $447_{13k}$ + $PEG_{0.8k}$-$44_{4k}$-$PEG_{0.8k}$ | 2:1 | 30 | 27.1 | 33.2 |
| | | 60 | 54.3 | 66.5 |
| | | 90 | 81.4 | 99.7 |
| $447_{13k}$ + $PEG_{0.8k}$-$44_{13k}$-$PEG_{0.8k}$ | 1:2 | 30 | 27.8 | 33.2 |
| | | 60 | 55.6 | 66.3 |
| | | 90 | 83.4 | 99.5 |
| $447_{13k}$ + $PEG_{0.8k}$-$44_{13k}$-$PEG_{0.8k}$ | 1:1 | 30 | 28.4 | 33.8 |
| | | 60 | 56.7 | 67.6 |
| | | 90 | 85.1 | 101.4 |
| $447_{13k}$ + $PEG_{0.8k}$-$44_{13k}$-$PEG_{0.8k}$ | 2:1 | 30 | 28.9 | 34.5 |
| | | 60 | 57.8 | 68.9 |
| | | 90 | 86.7 | 103.4 |
| $447_{13k}$ + $PEG_{5k}$-$44_{4k}$-$PEG_{5k}$ | 1:2 | 30 | 15.7 | 19.2 |
| | | 60 | 31.4 | 38.5 |
| | | 90 | 47.1 | 57.7 |
| $447_{13k}$ + $PEG_{5k}$-$44_{4k}$-$PEG_{5k}$ | 1:1 | 30 | 19.3 | 23.6 |
| | | 60 | 38.6 | 47.2 |
| | | 90 | 57.9 | 70.9 |
| $447_{13k}$ + $PEG_{5k}$-$44_{4k}$-$PEG_{5k}$ | 2:1 | 30 | 22.9 | 28.0 |
| | | 60 | 45.7 | 56.0 |
| | | 90 | 68.6 | 84.0 |

TABLE 2-continued

Chart for w/w to N/P conversion
($447_{13k}$ = 13 KDa MW ePBAE 447)

| Polymers | PBAE:PEG-PBAE w/w | Polymer:DNA w/w | Converted Polymer:DNA w/w | Converted N/P |
|---|---|---|---|---|
| $447_{13k}$ + $PEG_{5k}$-$44_{13k}$-$PEG_{5k}$ | 1:2 | 30 | 21.3 | 25.4 |
| | | 60 | 42.6 | 50.8 |
| | | 90 | 63.9 | 76.2 |
| $447_{13k}$ + $PEG_{5k}$-$44_{13k}$-$PEG_{5k}$ | 1:1 | 30 | 23.5 | 28.0 |
| | | 60 | 47.0 | 56.0 |
| | | 90 | 70.4 | 84.0 |
| $447_{13k}$ + $PEG_{5k}$-$44_{13k}$-$PEG_{5k}$ | 2:1 | 30 | 25.7 | 30.6 |
| | | 60 | 51.3 | 61.2 |
| | | 90 | 77.0 | 91.8 |
| $447_{13k}$ | No PEG-PBAE | 30 | 30 | 37.6 |
| | | 60 | 60 | 75.2 |
| | | 70 | 90 | 112.8 |

High-Throughput Evaluation of Uptake, Transfection and Cytotoxicity

High-throughput evaluation was sequentially performed at two levels to select the most optimized polyplex formulation based on uptake and transfection of polyplexes in H446 cells. Initially, PBAE polyplexes formed with 9 different ePBAEs were tested to select the best ePBAE polymer that would be blended with PEG-PBAE polymers in the subsequent screening. As shown in FIG. 7B, ePBAEs with more hydrophobic base polymer generally formed polyplexes with higher cytotoxicity, evidenced by B5S5 polyplexes leaving no viable cells 48 h after transfection. Higher uptake of ePBAE polyplexes with B4S5 base polymer did not result in a higher transfection rate than those with B4S4 base polymer, possibly due to different endocytosis pathways or rate-limiting downstream steps (FIGS. 7A, 7C, and 9). J. Kim, J. C. Sunshine, J. J. Green. Differential polymer structure tunes mechanism of cellular uptake and transfection routes of poly(beta-amino ester) polyplexes in human breast cancer cells Bioconjug Chem, 25 (2014):43-51. Top performing ePBAEs 444, 446, 447, and 457 with cell viability over 80% and transfection efficacies of 60-75% were blended into four selected PEG-PBAE polyplex formulations for subsequent evaluation.

As expected due to the shielding properties of PEG, the cellular uptake and transfection efficacy of PEG-PBAE polyplexes significantly decreased in comparison to unPEGylated PBAE polyplexes (FIGS. 8A, 8C, and 9). PEG-PBAE polyplexes formed with 5k-4k polymer generally resulted in higher uptake and transfection efficacies than 5k-13k polymer. Lower uptake of polyplexes with 5k-13k polymer is consistent with enhanced particle stability potentially from effective shielding of charge on the surface, which could in turn limit polyplexes' interaction with the cell membrane. Also, PEG-PBAE polyplexes blended with ePBAE 457 resulted in the highest uptake and transfection overall, which is comparable to the results from PBAE polyplex screening. This may be due to hydrophobicity of 457 that allows for stronger condensation and more stable particles. Specifically, PEG-PBAE polyplex formed from 457 blended with 5k-13k at 1:1 30 w/w condition was internalized in 30% of H446 cells, and transfected 40%. The higher measured transfection rate compared to the measured uptake rate is likely due to the lower sensitivity of measuring successful cellular uptake compared to successful gene expression (expressed plasmid leads to an amplified GFP florescence signal compared to the fluorescence signal from the labeled plasmid itself). This formulation also showed second highest geometric mean GFP fluorescence intensity, which is an indicator of the amount of protein expressed by the transgene per cell (FIG. 10).

Therapeutic Activity Against Small Cell Lung Cancer with PEG-PBAE/pHSV-tk Polyplexes and Ganciclovir Ganciclovir is a widely investigated prodrug of interest for suicide gene therapy for different types of cancer. A. Mangraviti, S. Y. Tzeng, K. L. Kozielski, Y. Wang, Y. Jin, D. Gullotti, et al. Polymeric nanoparticles for nonviral gene therapy extend brain tumor survival in vivo ACS Nano, 9 (2015):1236-49; P. D. Boucher, R. J. Ruch, D. S. Shewach. Differential ganciclovir-mediated cytotoxicity and bystander killing in human colon carcinoma cell lines expressing herpes simplex virus thymidine kinase Hum Gene Ther, 9 (1998):801-14; M. Shalev, D. Kadmon, B. S. Teh, E. B. Butler, E. Aguilar-Cordova, T. C. Thompson, et al. Suicide gene therapy toxicity after multiple and repeat injections in patients with localized prostate cancer J Urol, 163 (2000): 1747-50.

The nontoxic ganciclovir prodrug is phosphorylated into ganciclovir triphosphate by the HSV-tk gene product, which then disrupts DNA replication and causes cell death. L. Z. Rubsam, P. D. Boucher, P. J. Murphy, M. KuKuruga, D. S. Shewach. Cytotoxicity and accumulation of ganciclovir triphosphate in bystander cells cocultured with herpes simplex virus type 1 thymidine kinase-expressing human glioblastoma cells Cancer Res, 59 (1999):669-75; M. T. Tomicic, R. Thust, B. Kaina. Ganciclovir-induced apoptosis in HSV-1 thymidine kinase expressing cells: critical role of DNA breaks, Bcl-2 decline and caspase-9 activation Oncogene, 21 (2002):2141-53.

PEG-PBAE polyplexes were examined as a functional vehicle for small cell lung cancer gene therapy by delivering PEG-PBAE/pHSV-tk polyplexes followed by ganciclovir treatment. The optimal PEGPBAE polyplex formulation 457+5k-13k 1:1 30 w/w was chosen and was compared to 457 60 w/w PBAE polyplexes for transfection of both H446 human small cell lung cancer cells and IMR-90 human lung fibroblasts as a healthy control cell type. PBAE and PEG-PBAE polyplexes were able to kill 60% and 35% of cancer cells, respectively (FIG. 11). Interestingly, the level of cell death induced by two types of polyplexes correlated closely with their EGFP transfection efficacies of 73% and 43% (FIGS. 7A and 8A), but not with their EGFP geometric mean intensities of 170000 and 4000 RFUs (FIG. 11). The expression of HSV-TK, followed by treatment with ganciclovir, is expected to cause death of the transfected cell. A two-fold increase of the ganciclovir dosage had negligible effect on cell death, demonstrating that the exogenous gene expression of HSV-tk was the limiting factor determining cell killing.

The same PEG-PBAE and PBAE polyplexes showed different outcomes with IMR-90 human lung fibroblasts. First, polyplexes formed with 457 ePBAE complexed with pEGFP at 60 w/w had significant inherent cytotoxicity of 50% (FIG. 11B). This demonstrates the potential fragility of healthy human cells and the need for biocompatible, non-cytotoxic formulations. This concern with potential PBAE polyplex cytotoxicity is resolved when 457 ePBAE is blended with 5k-13k at 1:1 ratio, as evidenced by near 100% viability from pEGFP as well as pHSV-tk+0 μg/mL ganciclovir controls. This reduced cytotoxicity is likely due to a combination of less 457 ePBAE being used to form PEGPBAE polyplexes in comparison to non-PEGylated PBAE polyplexes of the same total w/w and due to PEG molecules shielding potentially unfavorable interaction between surface-exposed positively charged 457 and cellular components. In addition, the same PEG-PBAE/HSV-tk DNA polyplexes+ganciclovir system is more specific in promoting killing of human lung cancer H446 cells than healthy human lung IMR-90 fibroblasts; 15% of IMR-90 cells are killed at the 10 μg/mL ganciclovir dosage. Overall, these results show the potential of stable and effective PEG-PBAE polyplexes for lung cancer gene therapy.

Further, a representative schematic of PEG-PBAE copolymer micelle self-assembly in aqueous solution with a hydrophobic drug encapsulated is shown in FIG. 12. NMR analysis confirmed PEG conjugation to both ends of the PBAE base polymer by the absence of acrylate peaks (FIG. 13). The particles were characterized by sizing at 1 and 24 hr, by histogram of particle concentration, and by determination of zeta potential (mV) using DLS (FIG. 14A, FIG. 14B, and FIG. 14C). Representative TEM images are shown in FIG. 15. Spherical shaped micelles can be seen. There was limited aggregation, perhaps due to TEM sample preparation. Critical micelle concentration was determined using a plot showing the change in $I_{339}/I_{335}$ for pyrene as the concentration (mg/mL) for PEG-PBAE was increased (FIG. 16).

Example 9

Discussion

Nanoparticles, including polyplexes that are formed by electrostatic interaction between cationic polymer and negatively charged nucleic acids, that are intended to be used for systemic administration, need to overcome challenges of destabilization in physiological saline, adsorption of serum proteins, and aggregation post-administration, which all can lead to rapid clearance from the blood. Furthermore, colloidal stability at sub-400 nm diameter is critical for nanoparticles in cancer therapy to utilize passive targeting to tumors and their leaky vasculature via the enhanced permeation and retention (EPR) effect. S. D. Steichen, M. Caldorera-Moore, N. A. Peppas. A review of current nanoparticle and targeting moieties for the delivery of cancer therapeutics Eur J Pharm Sci, 48 (2013):416-27.

A new copolymer synthesized by conjugating the hydrophilic molecule PEG to selected PBAE base polymers provided steric hindrance to the resulting PEGPBAE polyplexes that minimized particle aggregation and maintained an effective size for the EPR effect. When formulating both PBAE and PEG-PBAE polyplexes, the N/P ratios used are relatively high in comparison to polyplexes of different polymers, such as PEI (Table S1). Non-degradable PEI, with its high charge density, becomes cytotoxic at higher N/P ratios unless it is modified with degradable moieties. S. Boeckle, K. von Gersdorff, S. van der Piepen, C. Culmsee, E. Wagner, M. Ogris. Purification of polyethylenimine polyplexes highlights the role of free polycations in gene transfer J Gene Med, 6 (2004):1102-11; M. R. Park, K. O. Han, I. K. Han, M. H. Cho, J. W. Nah, Y. J. Choi, et al. Degradable polyethylenimine-alt-poly(ethylene glycol) copolymers as novel gene carriers J Control Release, 105 (2005):367-80.

Two features of the PBAE chemical structure allows for polyplexes with much higher N/P ratios. Firstly, PBAE has repeated ester bonds along its backbone and hence is hydrolytically degradable into small bioeliminable units and thus much higher w/w ratios can be utilized. J. C. Sunshine, D. Y. Peng, J. J. Green. Uptake and transfection with polymeric nanoparticles are dependent on polymer end-group structure, but largely independent of nanoparticle physical and chemical properties Mol Pharm, 9 (2012):3375-83.

Secondly, most of PBAEs' positive charge is from tertiary amines, some of which are not protonated in the physiological range of pH 5.1-7.4. J. C. Sunshine, D. Y. Peng, J. J. Green. Uptake and transfection with polymeric nanoparticles are dependent on polymer end-group structure, but largely independent of nanoparticle physical and chemical properties Mol Pharm, 9 (2012):3375-83. Thus, N/P ratio is a function of pH and not the necessarily the same as the ratio of positive charges to negative charges within the polyplexes. This pH dependence of the PBAE polyplexes' charge is an important feature as it provides pH buffering capacity, protecting DNA in endosomes and promoting endosomal escape consistent with the proton sponge hypothesis, enabling successful transfection. J. J. Green, R. Langer, D. G. Anderson. A combinatorial polymer library approach yields insight into nonviral gene delivery Acc Chem Res, 41 (2008):749-59.

PEG-PBAE polyplexes have ePBAE blended in at different mass ratios of ePBAE to PEG-PBAE. Although PEG-PBAE polymer has tertiary amines along the backbone that can be protonated and associate with the DNA, the end-group structure of ePBAE has been implicated to serve important and complimentary functions. For example, different end-groups were found to regulate specific uptake mechanisms and downstream steps leading to successful transfection. J. C. Sunshine, D. Y. Peng, J. J. Green. Uptake and transfection with polymeric nanoparticles are dependent on polymer end-group structure, but largely independent of nanoparticle physical and chemical properties Mol Pharm, 9 (2012):3375-83; J. Kim, J. C. Sunshine, J. J. Green. Differential polymer structure tunes mechanism of cellular uptake and transfection routes of poly(beta-amino ester) polyplexes in human breast cancer cells Bioconjug Chem, 25 (2014): 43-51. PEGylating polyplexes of various polymers has been shown to affect cellular uptake and intracellular trafficking significantly, often reducing cellular uptake and gene delivery efficacy in vitro. S. Mishra, P. Webster, M. E. Davis. PEGylation significantly affects cellular uptake and intracellular trafficking of non-viral gene delivery particles Eur J Cell Biol, 83 (2004):97-111.

While residual positive charge on the surface can contribute to particle-cell interaction, the presence and exposure of select ePBAE in PEG-PBAE polyplexes can promote cellular uptake via specific pathways that leads to greater transfection. 457 ePBAE, which was selected from high-throughput screening to be blended into PEG-PBAE polyplexes, yielded results that were in agreement to previous literature, which showed high in vivo efficacy of 457 PBAE polyplexes in a subcutaneous H446 xenograft mice model. C. D. Kamat, R. B. Shmueli, N. Connis, C. M. Rudin, J. J. Green, C. L. Hann. Poly(beta-amino ester) nanoparticle delivery of TP53 has activity against small cell lung cancer in vitro and in vivo Mol Cancer Ther, 12 (2013):405-15.

Interestingly, the PEG-PBAE polyplexes used in this study were able to kill H446 small cell lung cancer cells more than IMR-90 lung fibroblasts through HSVtk/ganciclovir treatment. This cancer cell selectivity in efficacy is possibly due to a higher doubling rate of cancer cells than fibroblasts, since ganciclovir phosphorylated by HSVtk kills cells by disrupting DNA replication in actively dividing cells. L. Z. Rubsam, P. D. Boucher, P. J. Murphy, M. KuKuruga, D. S. Shewach. Cytotoxicity and accumulation of ganciclovir triphosphate in bystander cells cocultured with herpes simplex virus type 1 thymidine kinase-expressing human glioblastoma cells Cancer Res, 59 (1999):669-75.

However, another potential explanation is cancer specificity of the ePBAE polymer. Our group has previously showed that specific ePBAE structure (including the (3-Aminopropyl)-4-methylpiperazine (E7) end-group) leads to increased transfection in various tumor cells in comparison to the healthy cells in the same tissue. H. Guerrero-Cazares, S. Y. Tzeng, N. P. Young, A. O. Abutaleb, A. Quinones-Hinojosa, J. J. Green. Biodegradable polymeric nanoparticles show high efficacy and specificity at DNA delivery to human glioblastoma in vitro and in vivo ACS Nano, 8 (2014):5141-53; S. Y. Tzeng, L. J. Higgins, M. G. Pomper, J. J. Green. Student award winner in the Ph.D. category for the 2013 society for biomaterials annual meeting and exposition, april 10-13, 2013, Boston, Mass.: biomaterial-mediated cancer-specific DNA delivery to liver cell cultures using synthetic poly(beta-amino ester)s J Biomed Mater Res A, 101 (2013):1837-45.

Intriguingly, this ePBAE polyplex cancer cell transfection specificity with E7 is evident in corresponding tumor and non-tumor primary cell samples that show the same cell doubling time and have the same percentage of polyplex cellular uptake. H. Guerrero-Cazares, S. Y. Tzeng, N. P. Young, A. O. Abutaleb, A. Quinones-Hinojosa, J. J. Green. Biodegradable polymeric nanoparticles show high efficacy and specificity at DNA delivery to human glioblastoma in vitro and in vivo ACS Nano, 8 (2014):5141-53. Since the current PEG-PBAE polyplexes do not have an active targeting functionality, further modification for cancer targeting, such as conjugation of a targeting ligand to the polymer and/or insertion of a cancer-specific promoter in the plasmid DNA, can further enhance their therapeutic efficiency in cancer therapy. J. Kim, D. R. Wilson, C. G. Zamboni, J. J. Green. Targeted polymeric nanoparticles for cancer gene therapy J Drug Target, 23 (2015):627-41.

The presently disclosed subject matter demonstrates an important step in the design of non-viral vectors that utilize the PBAE platform. Through the synthesis of new PEGylated PBAE polymers and new PEG-PBAE/ePBAE formulations, stability was enhanced, non-specific cytotoxicity was prevented, and selective killing of small cell lung cancer cells was enabled.

Example 10

Summary

PBAEs are a class of cationic polymers that has been shown to transfect a wide range of cell types with high efficiency. In an effort to make more stable PBAE polyplexes, we synthesized PEG-PBAEs using thiolene Michael addition reaction and fabricated new polyplexes with blends of PEG-PBAEs and ePBAEs. After selecting the best performing ePBAEs through screening against cytotoxicity and transfection in small cell lung cancer cells (H446), PEG-PBAE polyplexes of varying conditions, including PEG-PBAE molecular weight, mass ratios of ePBAE to PEG-PBAE, and total polymer to DNA mass ratios, were further evaluated for nanoparticle size, stability, cytotoxicity and transfection efficacy. The most effective formulation consisted of ePBAE 457 blended with PEG-PBAE 5k-13k at 1:1 w/w ratio, and the total polymer mixed with DNA at a 30 w/w ratio for polyplex self-assembly. This PEG-PBAE formulation maintained its size under 300 nm over 24 h in physiological PBS and transfected 40% of H446 cells. When human lung cancer cells were transfected with HSV-tk using the optimized PEG-PBAE polyplex and subsequently treated with ganciclovir, 35% of the cells were killed in contrast to 15% cell death to healthy human lung fibroblasts (IMR-90). The present study used a novel method to synthesize PEGylated PBAE polymer and to formulate stable polyplexes that do not exhibit biomaterial-based cytotoxicity, can successfully transfect human lung cancer cells, and can induce their death via HSV-tk/ganciclovir prodrug gene therapy.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

D. G. Anderson, A. Akinc, N. Hossain, R. Langer. Structure/property studies of polymeric gene delivery using a library of poly(beta-amino esters) Mol Ther, 11 (2005): 426-34.

N. S. Bhise, K. J. Wahlin, D. J. Zack, J. J. Green. Evaluating the potential of poly(beta-amino ester) nanoparticles for reprogramming human fibroblasts to become induced pluripotent stem cells Int J Nanomedicine, 8 (2013):4641-58.

C. J. Bishop, T. M. Ketola, S. Y. Tzeng, J. C. Sunshine, A. Urtti, H. Lemmetyinen, et al. The effect and role of carbon atoms in poly(beta-amino ester)s for DNA binding and gene delivery J Am Chem Soc, 135(2013):6951-7.

S. Boeckle, K. von Gersdorff, S. van der Piepen, C. Culmsee, E. Wagner, M. Ogris. Purification of polyethylenimine polyplexes highlights the role of free polycations in gene transfer J Gene Med, 6 (2004):1102-11.

P. D. Boucher, R. J. Ruch, D. S. Shewach. Differential ganciclovir-mediated cytotoxicity and bystander killing in human colon carcinoma cell lines expressing herpes simplex virus thymidine kinase Hum Gene Ther, 9 (1998): 801-14.

A. M. Brade, I. F. Tannock. Scheduling of radiation and chemotherapy for limited-stage small-cell lung cancer: repopulation as a cause of treatment failure? J Clin Oncol, 24 (2006):1020-2.

S. W. Cho, F. Yang, S. M. Son, H. J. Park, J. J. Green, S. Bogatyrev, et al. Therapeutic angiogenesis using genetically engineered human endothelial cells J Control Release, 160 (2012):515-24.

J J Green, R. Langer, DG Anderson, "A combinatorial polymer library approach yields insight into nonviral gene delivery,"Acc Chem Res, 2008, 41(6): 749-759.

H. Guerrero-Cazares, S. Y. Tzeng, N. P. Young, A. O. Abutaleb, A. Quinones-Hinojosa, J. J. Green. Biodegradable polymeric nanoparticles show high efficacy and specificity at DNA delivery to human glioblastoma in vitro and in vivo ACS Nano, 8 (2014):5141-53.

T. J. Harris, J. J. Green, P. W. Fung, R. Langer, D. G. Anderson, S. N. Bhatia. Tissue-specific gene delivery via nanoparticle coating Biomaterials, 31 (2010):998-1006.

J. M. Harris, R. B. Chess. Effect of pegylation on pharmaceuticals Nat Rev Drug Discov, 2 (2003):214-21.

T. Hollon. Researchers and regulators reflect on first gene therapy death Nat Med, 6 (2000):6.

C. D. Kamat, R. B. Shmueli, N. Connis, C. M. Rudin, J. J. Green, C. L. Hann. Poly(beta-amino ester) nanoparticle delivery of TP53 has activity against small cell lung cancer in vitro and in vivo Mol Cancer Ther, 12 (2013): 405-15.

J. Kim, J. C. Sunshine, J. J. Green. Differential polymer structure tunes mechanism of cellular uptake and transfection routes of poly(beta-amino ester) polyplexes in human breast cancer cells Bioconjug Chem, 25 (2014): 43-51.

Kim, M. S., Hwang, S. J., Han, J. K., Choi, E. K., Park, H. J., Lee, D. S. pH-Responsive PEG-Poly(beta-amino ester) Block Copolymer Micelles with a Sharp Transition. Macromolecular Rapid Communications. 27(6), 2006.

J. Kim, D. R. Wilson, C. G. Zamboni, J. J. Green. Targeted polymeric nanoparticles for cancer gene therapy J Drug Target, 23 (2015):627-41.

J. Ko, K. Park, Y. S. Kim, M. S. Kim, J. K. Han, K. Kim, R. W. Park, I. S. Kim, H. K Song, D. S. Lee. Tumoral acidic extracellular pH targeting of pH-responsive MPEG-poly (β-amino ester) block copolymer micelles for cancer therapy, *J Controlled Release,* 2007, 123:109-115.

A. Mangraviti, S. Y. Tzeng, K. L. Kozielski, Y. Wang, Y. Jin, D. Gullotti, et al. Polymeric nanoparticles for nonviral gene therapy extend brain tumor survival in vivo ACS Nano, 9 (2015):1236-49.

S. Mishra, P. Webster, M. E. Davis. PEGylation significantly affects cellular uptake and intracellular trafficking of non-viral gene delivery particles Eur J Cell Biol, 83 (2004):97-111.

D. E. Owens, 3rd, N. A. Peppas. Opsonization, biodistribution, and pharmacokinetics of polymeric nanoparticles Int J Pharm, 307 (2006):93-102.

D. W. Pack, A. S. Hoffman, S. Pun, P. S. Stayton. Design and development of polymers for gene delivery Nat Rev Drug Discov, 4 (2005):581-93.

M. R. Park, K. O. Han, I. K. Han, M. H. Cho, J. W. Nah, Y. J. Choi, et al. Degradable polyethylenimine-alt-poly(ethylene glycol) copolymers as novel gene carriers J Control Release, 105 (2005):367-80.

A. Paumier, C. Le Pechoux. Radiotherapy in small-cell lung cancer: where should it go? Lung Cancer, 69 (2010):133-40.

E. Rodriguez, R. C. Lilenbaum. Small cell lung cancer: past, present, and future Curr Oncol Rep, 12 (2010):327-34.

L. Z. Rubsam, P. D. Boucher, P. J. Murphy, M. KuKuruga, D. S. Shewach. Cytotoxicity and accumulation of ganciclovir triphosphate in bystander cells cocultured with herpes simplex virus type 1 thymidine kinase-expressing human glioblastoma cells Cancer Res, 59 (1999):669-75.

Stefano Salmaso and Paolo Caliceti, "Stealth Properties to Improve Therapeutic Efficacy of Drug Nanocarriers," Journal of Drug Delivery, vol. 2013, Article ID 374252, 19 pages, 2013.

M. Shalev, D. Kadmon, B. S. Teh, E. B. Butler, E. Aguilar-Cordova, T. C. Thompson, et al. Suicide gene therapy toxicity after multiple and repeat injections in patients with localized prostate cancer J Urol, 163 (2000):1747-50.

R. Siegel, D. Naishadham, A. Jemal. Cancer statistics, 2012 C A Cancer J Clin, 62 (2012):10-29.

W. Song, Z. Tang, M. Li, S. Lv, H. Yu, L. Ma, X. Zhuang, X. Chen, "Tunable pH-sensitive Poly(β-amino ester)s Synthesized from Primary Amines and Diacrylates for Intracellular Drug Delivery,"*Macromol. Biosci.,* 2012, 12:1375-1383.

S. D. Steichen, M. Caldorera-Moore, N. A. Peppas. A review of current nanoparticle and targeting moieties for the delivery of cancer therapeutics Eur J Pharm Sci, 48 (2013):416-27.

J. C. Sunshine, D. Y. Peng, J. J. Green. Uptake and transfection with polymeric nanoparticles are dependent on polymer end-group structure, but largely independent of nanoparticle physical and chemical properties Mol Pharm, 9 (2012):3375-83.

J. C. Sunshine, M. I. Akanda, D. Li, K. L. Kozielski, J. J. Green. Effects of base polymer hydrophobicity and end-group modification on polymeric gene delivery Biomacromolecules, 12 (2011):3592-600.

M. T. Tomicic, R. Thust, B. Kaina. Ganciclovir-induced apoptosis in HSV-1 thymidine kinase expressing cells: critical role of DNA breaks, Bcl-2 decline and caspase-9 activation Oncogene, 21 (2002):2141-53.

S. Y. Tzeng, J. J. Green. Subtle changes to polymer structure and degradation mechanism enable highly effective nanoparticles for siRNA and DNA delivery to human brain cancer Adv Healthc Mater, 2 (2013):468-80.

S. Y. Tzeng, L. J. Higgins, M. G. Pomper, J. J. Green. Student award winner in the Ph.D. category for the 2013 society for biomaterials annual meeting and exposition, april 10-13, 2013, Boston, Mass.: biomaterial-mediated cancer-specific DNA delivery to liver cell cultures using synthetic poly(beta-amino ester)s J Biomed Mater Res A, 101 (2013):1837-45.

Vandenbergh, J., Ranieri, K., Junkers, T. Synthesis of (Bio)-Degradable Poly(beta-thioester)s via Amine Catalyzed Thiolene Click Polymerization. Macromolecular Chemistry and Physics. 213(24), 2611-7 (2012).

R. E. Vandenbroucke, B. G. DeGeest, S. Bonne, M. Vinken, T. Van Haecke, H. Heimberg, et al. Prolonged gene silencing in hepatoma cells and primary hepatocytes after small interfering RNA delivery with biodegradable poly (beta-amino esters) J Gene Med, 10 (2008):783-94.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A particle comprising a blend of a poly(β-amino ester) (PBAE) and a-polyethylene glycol (PEG)-b-poly(β-amino ester) (PBAE) co-polymer (PEG-PBAE) of Formula (I):

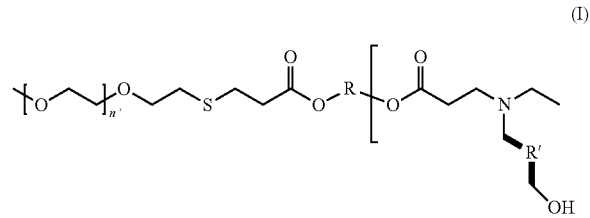

(I)

-continued

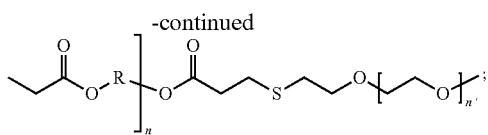

wherein:
  each n and n' is independently an integer from 1 to 10,000, 1 to 1,000, 1 to 100, 1 to 30, 5 to 20, 10 to 15, and 1 to 10;
  R is $C_2$ to $C_8$ substituted or unsubstituted linear or branched alkylene; and
  R' is $C_1$ to $C_5$ substituted or unsubstituted linear or branched alkylene;
  wherein each R and R' can independently be the same or different; and
  wherein the poly(β-amino ester) (PBAE) is:

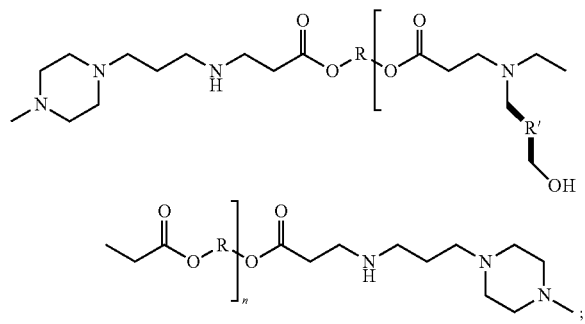

wherein R' is $C_1$ to $C_5$ substituted or unsubstituted linear or branched alkylene;
  and pharmaceutically acceptable salts thereof.

2. The particle of claim 1, wherein the PEG subunit of the PEG-PBAE co-polymer has a molecular weight selected from the group consisting of about 0.5 kDa to about 5 kDa, about 5 kDa to about 10 kDa, about 10 kDa to about 20 kDa, and about 20 kDa to about 30 kDa.

3. The particle of claim 1, wherein the PBAE subunit of the PEG-PBAE co-polymer has a molecular weight ranging from about 4 kDa to about 13 kDa.

4. The particle of claim 1, wherein the PEG-PBAE co-polymer is selected from the group consisting of: $PEG_{0.8k}$-B4S4$_{4k}$-$PEG_{0.8k}$, $PEG_{0.8k}$-B4S4$_{13k}$-$PEG_{0.8k}$, $PEG_{5k}$-B4S4$_{4k}$-$PEG_{5k}$, and $PEG_{5k}$-B4S4$_{13k}$-$PEG_{5k}$.

5. The particle of claim 1, further comprising a cargo.

6. The particle of claim 5, wherein the cargo is selected from a gene, DNA, RNA, siRNA, miRNA, isRNA, agRNA, smRNA, a nucleic acid, a peptide, a protein, a chemotherapeutic agent, a hydrophobic drug, and a small molecule drug.

7. The particle of claim 6, wherein the cargo is selected from a gene, DNA, and siRNA.

8. The particle of claim 7, wherein the cargo is DNA and the DNA is present in the blend of PBAE and PEG-PBAE at a blend:DNA ratio between about 30 w/w to about 90 w/w.

9. The particle of claim 1, wherein the PBAE comprises the subunits B4, S4, and E7 (447) or B4, S5, and E7 (457) and the PEG-PBAE is $PEG_{(0.5k-5k)}$-B4S4$_{(4k-13k)}$-$PEG_{(0.5k-5k)}$ or $PEG_{(0.5k-5k)}$-B4S5$_{(4k-13k)}$-$PEG_{(0.5k-5k)}$.

10. The particle of claim 9, wherein the PBAE is 447 or 457 and the PEG-PBAE is selected from $PEG_{0.8k}$-B4S4$_{13k}$-$PEG_{0.8k}$, $PEG_{5k}$-B4S4$_{13k}$-$PEG_{5k}$, $PEG_{0.8k}$-B4S5$_{13k}$-$PEG_{0.8k}$ or $PEG_{5k}$-B4S5$_{13k}$-$PEG_{5k}$.

11. The particle of claim 1, comprising a weight-to-weight ratio of PBAE to PEG-PBAE-PEG of between about 1:2 to about 2:1.

12. The particle of claim 11, wherein the weight-to-weight ratio of PBAE to PEG-PBAE-PEG is about 1:1.

13. A method for treating a disease or condition, the method comprising administering to a subject in need of treatment thereof, a particle of claim 1 or a pharmaceutical composition thereof, comprising a pharmaceutical or therapeutic agent effective for treating the disease or condition.

14. The method of claim 13, wherein the disease or condition is selected from the group consisting of cancer, cardiovascular diseases, infectious diseases, and ophthalmic diseases.

15. The method of claim 14, wherein the cancer is selected from the group consisting of brain cancer, lung cancer, breast cancer, prostate cancer, and colorectal cancer.

16. The method of claim 15, wherein the brain cancer is Glioblastoma Multiforme.

17. The method of claim 14, wherein the ophthalmic disease is age-related macular degeneration.

18. A method for delivering a therapeutic agent to a cell, a cell line, a tissue, or an organism, the method comprising associating a pharmaceutical or therapeutic agent with a blend of a poly(β-amino ester) (PBAE) and a polyethylene glycol (PEG)-b-poly(β-amino ester) (PBAE) co-polymer (PEG-PBAE) of Formula (I) of claim 1, or a pharmaceutical composition thereof, to form one or more particles, micelles, or polyplexes comprising the agent and the blend of a poly(β-amino ester) (PBAE) and a polyethylene glycol (PEG)-b-poly(β-amino ester) (PBAE) co-polymer (PEG-PBAE), and administering the one or more particles or contacting the one or more particles with the cell, cell line, tissue or organism.

19. The method of claim 18, wherein the therapeutic agent is selected from the group consisting of a gene, DNA, RNA, siRNA, miRNA, isRNA, agRNA, smRNA, a nucleic acid, a peptide, a protein, a chemotherapeutic agent, a hydrophobic drug, and a small molecule drug.

20. The method of claim 18, wherein the cell comprises a cancer cell.

21. The method of claim 20, wherein the cancer cell comprises a breast cancer cell.

* * * * *